United States Patent
Le Bourdelles et al.

[11] Patent Number: 6,130,058
[45] Date of Patent: Oct. 10, 2000

[54] HUMAN NMDA R2A RECEPTOR SUBUNIT AND ISOFORMS OF THE HUMAN NMDA-R1 RECEPTOR SUBUNIT AND ENCODING CDNAS

[75] Inventors: Beatrice Le Bourdelles, Sawbridgeworth; Janice Ann Myers, Chingford; Paul John Whiting, Stansted Mountfitchet, all of United Kingdom

[73] Assignee: Merck Sharpe & Dohme Ltd., Hoddesdon, United Kingdom

[21] Appl. No.: 08/436,332

[22] PCT Filed: Nov. 11, 1993

[86] PCT No.: PCT/GB93/02324

§ 371 Date: May 10, 1995

§ 102(e) Date: May 10, 1995

[87] PCT Pub. No.: WO94/11501

PCT Pub. Date: May 26, 1994

[30] Foreign Application Priority Data

Nov. 12, 1992 [GB] United Kingdom .................. 9223769
Apr. 2, 1993 [GB] United Kingdom .................. 9307026

[51] Int. Cl.[7] ........................ C12N 15/12; C07K 14/705
[52] U.S. Cl. ...................... 435/69.1; 536/23.5; 536/23.1; 530/350; 435/320.1
[58] Field of Search ........................ 435/7.1, 7.2, 69.1, 435/252.3, 320.1, 325; 530/350; 536/23.1, 23.5

[56] References Cited

FOREIGN PATENT DOCUMENTS

WO 93/23536  11/1993  WIPO .

OTHER PUBLICATIONS

Monyer, et al., "Heteromeric NMDA receptors: molecular and functional distinction of subtypes", Science, vol. 256, May 22, 1992, pp. 1217–1221.

Meguro, et al., "Functional characterization of a heteromeric NMDA receptor channel expressed from cloned cDNAs", Nature, vol. 357, May 7, 1992, pp. 70–74.

Nakanishi, et al., "Alternative spicing generates functionally distinct N–methyl–D–aspartate receptors", Proc. of Nat. Acad. of Sci., vol. 89, Sep. 1992, pp. 8552–8556.

Sugihara, et al., "Structures and properties of seven isoforms of the NMDA receptor generated by alternative splicing", Biochem. & Biophy. Res. Comm., vol. 185, No. 3, Jun. 1992, pp. 826–832.

Jansen et al., Autoradiographic visualisation of [3H]DTG binding to sigma receptors, [3H]TCP binding sites, and L–[3H]glutamate binding to NMDA receptors in human cerebellum, Neurosci. Lett., 12: 143–146, 1991.

Tanabe et al., A family of metabotropic glutamate receptors, Neuron, 8: 169–179, Jan. 1992.

Albert et al, *J. Biol. Chem.* 265(10): 5825–5832, Apr. 5, 1990.

Puckett et al., *P.N.A.S.* 88:7557–7561, Sep. 1991.

Sun et al, *P.N.A.S.* 89:1443–1447, Feb. 1992.

Grenningloh et al, *EMBO J.* 9(3):771–776, Mar. 1990.

Schofield et al, *FEBS Letts* 244(2):361–364, Feb. 1989.

Grandy et al, *P.N.A.S.* 86:9762–9766, Dec. 1989.

Zhou et al, *Nature* 347:76–80, Sep. 6, 1990.

*Primary Examiner*—Lorraine Spector
*Assistant Examiner*—Claire M. Kaufman
*Attorney, Agent, or Firm*—Michael D. Yablonsky; Jack L. Tribble

[57] ABSTRACT

The present invention relates to a stably co-transfected eukaryotic cell line that expresses an N-methyl-D-aspartate (NMDA) receptor, particularly a human NMDA receptor, which receptor comprises at least one R1 subunit isoform, or at least one R1 subunit isoform and one or two R2 subunits. Additionally, the cell line can be used to design and develop NMDA receptor subtype-selective compounds. The invention also relates to cloning of novel cDNA sequences encoding the human NMDAR 2A subunit and various isoforms of the human NMDA R1 subunit.

4 Claims, 19 Drawing Sheets

```
                                            gccgcgcagagccaggcccgcggcccgagccc   -31
_____SP_____18_
Met Ser Thr Met Arg Leu Leu Thr Leu Ala Leu Leu Phe Ser Cys Ser Leu Ala
ATG AGC ACC ATG CGC CTG TTG ACG CTC GCC CTG CTG TTC TCC TGC TCC CTC GCC     54

36
Arg Ala Ala Cys Asp Pro Lys Ile Val Asn Ile Gly Ala Val Leu Ser Thr Arg
CGT GCC GCG TGC GAC CCC AAG ATC GTC AAC ATT GGC GCG GTG CTG AGC ACG CGG    108

54
Lys His Glu Gln Met Phe Arg Glu Ala Val Asn Gln Ala Asn Lys Arg His Gly
AAG CAC GAG CAG ATG TTC CGC GAG GCC GTG AAC CAG GCC AAC AAG CGG CAC GGC    152

72
Ser Trp Lys Ile Gln Leu Asn Ala Thr Ser Val Thr His Lys Pro Asn Ala Ile
TCC TGG AAG ATT CAG CTC AAT GCC ACC TCC GTC ACG CAC AAG CCC AAC GCC ATC    216

90
Gln Met Ala Leu Ser Val Cys Glu Asp Leu Ile Ser Ser Gln Val Tyr Ala Ile
CAG ATG GCT CTG TCG GTG TGC GAG GAC CTC ATC TCC AGC CAG GTC TAC GCC ATC    270

108
Leu Val Ser His Pro Pro Thr Pro Asn Asp His Phe Thr Pro Thr Pro Val Ser
CTA GTT AGC CAT CCA CCT ACC CCC AAC GAC CAC TTC ACT CCC ACC CCT GTC TCC    324

126
Tyr Thr Ala Gly Phe Tyr Arg Ile Pro Val Leu Gly Leu Thr Thr Arg Met Ser
TAC ACA GCC GGC TTC TAC CGC ATA CCC GTG CTG GGG CTG ACC ACC CGC ATG TCC    378

144
Ile Try Ser Asp Lys Ser Ile His Leu Ser Phe Leu Arg Thr Val Pro Pro Tyr
ATC TAC TCG GAC AAG AGC ATC CAC CTG AGC TTC CTG CGC ACC GTG CCG CCC TAC    432

162
Ser His Gln Ser Ser Val Trp Phe Glu Met Met Arg Val Tyr Ser Trp Asn His
TCC CAC CAG TCC AGC GTG TGG TTT GAG ATG ATG CGT GTC TAC AGC TGG AAC CAC    485

180
Ile Ile Leu Leu Val Ser Asp Asp His Glu Gly Arg Ala Ala Gln Lys Arg Leu
ATC ATC CTG CTG GTC AGC GAC GAC CAC GAG GGC CGG GCG GCT CAG AAA CGC CTG    540
```

FIG.2A

```
                                                                    198
Glu Thr Leu Leu Glu Glu Arg Glu Ser Lys Ala Glu Lys Val Leu Gln Phe Asp
GAG ACG CTG CTG GAG GAG CGT GAG TCC AAG GCA GAG AAG GTG CTG CAG TTT GAC   594

216
Pro Gly Thr Lys Asn Val Thr Ala Leu Leu Met Glu Ala Lys Glu Leu Glu Ala
CCA GGG ACC AAG AAC GTG ACG GCC CTG CTG ATG GAG GCG AAA GAG CTG GAG GCC   648

234
Arg Val Ile Ile Leu Ser Ala Ser Glu Asp Asp Ala Ala Thr Val Tyr Arg Ala
CGG GTC ATC ATC CTT TCT GCC AGC GAG GAC GAT GCT GCC ACT GTA TAC CGC GCA   702

252
Ala Ala Met Leu Asn Met Thr Gly Ser Gly Tyr Val Trp Leu Val Gly Glu Arg
GCC GCG ATG CTG AAC ATG ACG GGC TCC GGG TAC GTG TGG CTG GTC GGC GAG CGC   756

270
Glu Ile Ser Gly Asn Ala Leu Ala Tyr Ala Pro Asp Gly Ile Leu Gly Leu Gln
GAG ATC TCG GGG AAC GCC CTG GCC TAC GCC CCA GAC GGC ATC CTC GGG CTG CAG   810

288
Leu Ile Asn Gly Lys Asn Glu Ser Ala His Ile Ser Asp Ala Val Gly Val Val
CTC ATC AAC GGC AAG AAC GAG TCG GCC CAC ATC AGC GAC GCC GTG GGC GTG GTG   864

306
Ala Gln Ala Val His Glu Leu Leu Glu Lys Glu Asn Ile Thr Asp Pro Pro Arg
GCC CAG GCC GTG CAC GAG CTC CTC GAG AAG GAG AAC ATC ACC GAC CCG CCG CGG   918

324
Gly Cys Val Gly Asn Thr Asn Ile Trp Lys Thr Gly Pro Leu Phe Lys Arg Val
GGC TGC GTG GGC AAC ACC AAC ATC TGG AAG ACC GGG CCG CTC TTC AAG AGA GTG   972

342
Leu Met Ser Ser Lys Tyr Ala Asp Gly Val Thr Gly Arg Val Glu Phe Asn Glu
CTG ATG TCT TCC AAG TAT GCG GAT GGG GTG ACT GGT CGC GTG GAG TTC AAT GAG  1026

360
Asp Gly Asp Arg Lys Phe Ala Asn Tyr Ser Ile Met Asn Leu Gln Asn Arg Lys
GAT GGG GAC CGG AAG TTC GCC AAC TAC AGC ATC ATG AAC CTG CAG AAC CGC AAG  1080

378
Leu Val Gln Val Gly Ile Tyr Asn Gly Thr His Val Ile Pro Asn Asp Arg Lys
CTG GTG CAA GTG GGC ATC TAC AAT GGC ACC CAC GTC ATC CCT AAT GAC AGG AAG  1134
```

FIG.2B

```
                                                                      396
Ile Ile Trp Pro Gly Gly Glu Thr Glu Lys Pro Arg Gly Tyr Gln Met Ser Thr
ATC ATC TGG CCA GGC GGA GAG ACA GAG AAG CCT CGA GGG TAC CAG ATG TCC ACC   1188

414
Arg Leu Lys Ile Val Thr Ile His Gln Glu Pro Phe Val Tyr Val Lys Pro Thr
AGA CTG AAG ATT GTG ACG ATC CAC CAG GAG CCC TTC GTG TAC GTC AAG CCC ACG   1242

432
Leu Ser Asp Gly Thr Cys Lys Glu Glu Phe Thr Val Asn Gly Asp Pro Val Lys
CTG AGT GAT GGG ACA TGC AAG GAG GAG TTC ACA GTC AAC GGC GAC CCA GTC AAG   1295

450
Lys Val Ile Cys Thr Gly Pro Asn Asp Thr Ser Pro Gly Ser Pro Arg His Thr
AAG GTG ATC TGC ACC GGG CCC AAC GAC ACG TCG CCG GGC AGC CCC CGC CAC ACG   1350

468
Val Pro Gln Cys Cys Try Gly Phe Cys Ile Asp Leu Leu Ile Lys Leu Ala Arg
GTG CCT CAG TGT TGC TAC GGC TTT TGC ATC GAC CTG CTC ATC AAG CTG GCA CGG   1404

486
Thr Met Asn Phe Thr Tyr Glu Val His Leu Val Ala Asp Gly Lys Phe Gly Thr
ACC ATG AAC TTC ACC TAC GAG GTG CAC CTG GTG GCA GAT GGC AAG TTC GGC ACA   1458

504
Gln Glu Arg Val Asn Asn Ser Asn Lys Lys Glu Trp Asn Gly Met Met Gly Glu
CAG GAG CGG GTG AAC AAC AGC AAC AAG AAG GAG TGG AAT GGG ATG ATG GGC GAG   1512

522
Leu Leu Ser Gly Gln Ala Asp Met Ile Val Ala Pro Leu Thr Ile Asp Asp Glu
CTG CTC AGC GGG CAG GCA GAC ATG ATC GTG GCG CCG CTA ACC ATA AAC AAC GAG   1566

540
Arg Ala Gln Tyr Ile Glu Phe Ser Lys Pro Phe Lys Tyr Gln Gly Leu Thr Ile
CGC GCG CAG TAC ATC GAG TTT TCC AAG CCC TTC AAG TAC CAG GGC CTG ACT ATT   1620

558
Leu Val Lys Lys Glu Ile Pro Arg Ser Thr Leu Asp Ser Phe Met Gln Pro Phe
CTG GTC AAG AAG GAG ATT CCC CGG AGC ACG CTG GAC TCG TTC ATG CAG CCG TTC   1674
```

FIG.2C

```
                                                  _____TM1_____   576
Gln Ser Thr Leu Trp Leu Leu Val Gly Leu Ser Val His Val Val Ala Val Met
CAG AGC ACA CTG TGG CTG CTG GTG GGG CTG TCG GTG CAC GTG GTG GCC GTG ATG   1728

_____                                                           594
Leu Tyr Leu Leu Asp Arg Phe Ser Pro Phe Gly Arg Phe Lys Val Asn Ser Glu
CTG TAC CTG CTG GAC CGC TTC AGC CCC TTC GGC CGG TTC AAG GTG AAC AGC GAG   1782

_____TM2_____            612
Glu Glu Glu Glu Asp Ala Leu Thr Leu Ser Ser Ala Met Trp Phe Ser Trp Gly
GAG GAG GAG GAG GAC GCA CTG ACC CTG TCC TCG GCC ATG TGG TTC TCC TGG GGC   1836

_____                                         630
Val Leu Leu Asn Ser Gly Ile Gly Glu Gly Ala Pro Arg Ser Phe Ser Ala Arg
GTC CTG CTC AAC TCC GGC ATC GGG GAA GGC GCC CCC AGA AGC TTC TCA GCG CGC   1890

_____TM3_____            648
Ile Leu Gly Met Val Trp Ala Gly Phe Ala Met Ile Ile Val Ala Ser Tyr Thr
ATC CTG GGC ATG GTG TGG GCC GGC TTT GCC ATG ATC ATC GTG GCC TCC TAC ACT   1944

___                                                                       666
Ala Asn Leu Ala Ala Phe Leu Val Leu Asp Arg Pro Glu Glu Arg Ile Thr Gly
GCC AAC TTG GCG GCC TTC CTG GTG CTG GAC CGG CCG GAG GAG CGC ATC ACG GGC   1998

684
Ile Asn Asp Pro Arg Leu Arg Asn Pro Ser Asp Lys Phe Ile Tyr Ala Thr Val
ATC AAC GAC CCT CGG CTG AGG AAC CCC TCG GAC AAG TTT ATC TAC GCC ACG GTG   2052

702
Lys Gln Ser Ser Val Asp Ile Tyr Phe Arg Arg Gln Val Glu Leu Ser Thr Met
AAG CAG AGC TCC GTG GAT ATC TAC TTC CGG CGC CAG GTG GAG CTG AGC ACC ATG   2106

720
Tyr Arg His Met Glu Lys His Asn Tyr Glu Ser Ala Ala Glu Ala Ile Gln Ala
TAC CGG CAT ATG GAG AAG CAC AAC TAC GAG AGT GCG GCG GAG GCC ATC CAG GCC   2160

738
Val Arg Asp Asn Lys Leu His Ala Phe Ile Trp Asp Ser Ala Val Leu Glu Phe
GTG AGA GAC AAC AAG CTG CAT GCC TTC ATC TGG GAC TCG GCG GTG CTG GAG TTC   2214

756
Glu Ala Ser Gln Lys Cys Asp Leu Val Thr Thr Gly Glu Leu Phe Phe Arg Ser
GAG GCC TCG CAG AAG TGC GAC CTG GTG ACG ACT GGA GAG CTG TTT TTC CGC TCG   2268
```

FIG.2D

```
                                                                              774
Gly Phe Gly Ile Gly Met Arg Lys Asp Ser Pro Trp Lys Gln Asn Val Ser Leu
GGC TTC GGC ATA GGC ATG CGC AAA GAC AGC CCC TGG AAG CAG AAC GTC TCC CTG  2322

792
Ser Ile Leu Lys Ser His Glu Asn Gly Phe Met Glu Asp Leu Asp Lys Thr Trp
TCC ATC CTC AAG TCC CAC GAG AAT GGC TTC ATG GAA GAC CTG GAC AAG ACG TGG  2376

810
Val Arg Tyr Gln Glu Cys Asp Ser Arg Ser Asn Ala Pro Ala Thr Leu Thr Phe
GTT CGG TAT CAG GAA GTG GAC TCG CGC AGC AAC GCC CCT GCA ACC CTT ACT TTT  2430

_____ TM4 _____        828
Glu Asn Met Ala Gly Val Phe Met Leu Val Ala Gly Gly Ile Val Ala Gly Ile
GAG AAC ATG GCC GGG GTC TTC ATG CTG GTA GCT GGG GGC ATC GTG GCC GGG ATC  2484

_____                                                        845
Phe Leu Ile Phe Ile Glu Ile Ala Tyr Lys Arg His Lys Asp Ala Arg Arg Lys
TTC CTG ATT TTC ATC GAG ATT GCC TAC AAG CGG CAC AAG GAT GCT CGC CGG AAG  2538

864
Gln Met Gln Leu Ala Phe Ala Ala Val Asn Val Trp Arg Lys Asn Leu Gln Gln
CAG ATG CAG CTG GCC TTT GCC GCC GTT AAC GTG TGG CGG AAG AAC CTG CAG CAG  2592

882
Tyr His Pro Thr Asp Ile Thr Gly Pro Leu Asn Leu Ser Asp Pro Ser Val Ser
TAC CAT CCC ACT GAT ATC ACG GGC CCG CTC AAC CTC TCA GAT CCC TCG GTC AGC  2645

885
Thr Val Val
ACC GTG GTG tga ggccccggagcgcccacctgcccagtttagcccggc
```

FIG.2E

NMDA R1a:

```
       863                864                   900      901                     938
       Asn Leu Gln        Asp Arg Lys.....Lys Asp Thr    Ser Thr Gly.......Arg Glu Ser
       AAC CTG CAG        GAT AGA AAG.....AAA GAC ACG    AGC ACC GGG.......AGG GAG AGCtga gactc .....
       2589               2592            2700           2703
                          |_____deletion 1_____|   |_____deletion 2_____|
```

NMDA R1d:

```
       863                864                   900      901                     922
       Asn Leu Gln        Asp Arg Lys.....Lys Asp Thr    Gln Tyr His.......Thr Val Val
       AAC CTG CAG        GAT AGA AAG.....AAA GAC ACG    CAG TAC CAT.......ACC GTG GTGtga ggcccc .....
       2589               2592            2700           2703
                          |_____deletion 1_____|   |_____alternate sequence_____|
```

NMDA R1e:

```
       863                864                     885
       Asn Leu Gln        Gln Tyr His.......Thr Val Val
       AAC CTG CAG        CAG TAC CAT.......ACC GTG GTGtga ggcc .....
       2589               2592
                          |_____alternate sequence_____|
```

FIG.3A

```
                864
deletion 1:     Asp Arg Lys Ser Gly Arg Ala Glu Pro Asp Pro Lys Lys Lys Ala Thr
                GAT AGA AAG AGT GGT AGA GCA GAG CCT GAC CCT AAA AAG AAA GCC ACA
                2592

Phe Arg Ala Ile Thr Ser Thr Leu Ala Ser Ser Phe Lys Arg Arg Arg
                TTT AGG GCT ATC ACC TCC ACC CTG GCT TCC AGC TTC AAG AGG CGT AGG

900
                Ser Ser Lys Asp Thr
                TCC TCC AAA GAC ACG
                                2700

901
deletion 2:     Ser Thr Gly Gly Gly Arg Gly Ala Leu Gln Asn Gln Lys Asp Thr Val
                AGC ACC GGG GGT GGA CGC CCG GCT TTG CAA AAC CAA AAA GAC ACA GTG
                2703

Leu Pro Arg Arg Pro Ile Glu Arg Glu Glu Gly Gln Leu Gln Leu Cys
                CTG CCG CGA CGG CCT ATT GAG AGG GAG GAG GGC CAG CTG CAG CTG TGT

938
                Ser Arg His Arg Glu Ser
                TCC CGT CAT AGG GAG AGC tga gactccccgcccgccctcctctgccccccctccccc gcagacagacagacagacggacgggacagcgg 864
alternate       Gln Tyr His Pro Thr Asp Ile Thr Gly Pro Leu Asn Leu Ser Asp Pro
sequence :      CAG TAC CAT CCC ACT GAT ATC ACG GGC CCG CTC AAC CTC TCA GAT CCC
                2592
                                    885
                Ser Val Ser Thr Val Val
                TCG GTC AGC ACC GTG GTG tga ggccccggagcgcccacctgcccagtttagccc
```

FIG.3B

```
             10          20          30          40         49         58
                                                              >   ___  ___  ___
CTGCATCCTC  GACCTTCTCG  GGCTACAGGG  ACCGTCAGTG  GCGACT  ATG  GGC  AGA  GTG  GGC
                                                        Met  Gly  Arg  Val  Gly 67          76          85          94          103         112
       ___         ___         ___         ___         ___         ___
TAT  TGG  ACC  CTG  CTG  GTG  CTG  CCG  GCC  CTT  CTG  GTC  TGG  CGC  GGT  CCG  GCG  CCG
Tyr  Trp  Thr  Leu  Leu  Val  Leu  Pro  Ala  Leu  Leu  Val  Trp  Arg  Gly  Pro  Ala  Pro 121         130         139         148         157         166
AGC  GCG  GCG  GCG  GAG  AAG  GGT  CCC  CCC  GCG  CTA  AAT  ATT  GCG  GTG  ATG  CTG  GGT
Ser  Ala  Ala  Ala  Glu  Lys  Gly  Pro  Pro  Ala  Leu  Asn  Ile  Ala  Val  MET  Leu  Gly 175         184         193         202         211         220
CAC  AGC  CAC  GAC  GTG  ACA  GAG  CGC  GAA  CTT  CGA  ACA  CTG  TGG  GGC  CCC  GAG  CAG
His  Ser  His  Asp  Val  Thr  Glu  Arg  Glu  Leu  Arg  Thr  Leu  Trp  Gly  Pro  Glu  Gln 229         238         247         256         265         274
GCG  GGC  GGG  CTG  CCC  CTG  GAC  GTG  AAC  GTG  GTA  GCT  CTG  CTG  ATG  AAC  CGC  ACC
Ala  Gly  Gly  Leu  Pro  Leu  Asp  Val  Asn  Val  Val  Ala  Leu  Leu  MET  Asn  Arg  Thr 283         292         301         310         319         328
GAC  CCC  AAG  AGC  CTC  ATC  ACG  CAC  GTG  TGC  GAC  CTC  ATG  TCC  GGG  GCA  CGC  ATC
Asp  Pro  Lys  Ser  Leu  Ile  Thr  His  Val  Cys  Asp  Leu  MET  Ser  Gly  Ala  Arg  Ile 337         346         355         364         373         382
CAC  GGC  CTC  TGT  TTT  GGG  GAC  GAC  ACG  GAC  CAG  GAG  GTC  GTA  GCC  CAG  ATG  CTG
His  Gly  Leu  Val  Phe  Gly  Asp  Asp  Thr  Asp  Gln  Glu  Val  Val  Ala  Gln  MET  Leu 391         400         409         418         427         436
GAT  TTT  ATC  TCC  TCC  CAC  ACC  TTC  GTC  CCC  ATC  TTG  GGC  ATT  CAT  GGG  GGC  GCA
Asp  Phe  Ile  Ser  Ser  His  Thr  Phe  Val  Pro  Ile  Leu  Gly  Ile  His  Gly  Gly  Ala 445         454         463         472         481         490
TCT  ATG  ATC  ATG  GCT  GAC  AAG  GAT  CCG  ACG  TCT  ACC  TTC  TTC  CAG  TTT  GGA  GCG
Ser  MET  Ile  MET  Ala  Asp  Lys  Asp  Pro  Thr  Ser  Thr  Phe  Phe  Gln  Phe  Gly  Ala
```

FIG.4A

```
    499             508             517             526             535             544
TCC ATC CAG CAG CAA GCC ACG GTC ATG CTG AAG ATC ATG CAG GAC TAT GAC TGG
Ser Ile Gln Gln Gln Ala Thr Val MET Leu Lys Ile MET Gln Asp Tyr Asp Trp 553             562             571             580             589             598
CAT GTC TTC TCC CTG GTG ACC ACT ATC TTC CCT GGC TAC AGG GAA TTC ATC AGC
His Val Phe Ser Leu Val Thr Thr Ile Phe Pro Gly Tyr Arg Glu Phe Ile Ser 607             616             625             634             643             652
TTC GTC AAG ACC ACA GTG GAC AAC AGC TTT GTG GGC TGG GAC ATG CAG AAT GTG
Phe Val Lys Thr Thr Val Asp Asn Ser Phe Val Gly Trp Asp MET Gln Asn Val 661             670             679             688             697             706
ATC ACA CTG GAC ACT TCC TTT GAG GAT GCA AAG ACA CAA GTC CAG CTG AAG AAG
Ile Thr Leu Asp Thr Ser Phe Glu Asp Ala Lys Thr Gln Val Gln Leu Lys Lys 715             724             733             742             751             760
ATC CAC TCT TCT GTC ATC TTG CTC TAC TGT TCC AAA GAC GAG GCT GTT CTC ATT
Ile His Ser Ser Val Ile Leu Leu Tyr Cys Ser Lys Asp Glu Ala Val Leu Ile 769             778             787             796             805             814
CTG AGT GAG GCC CGC TCC CTT GGC GTC ACC GGG TAT GAT TTC TTC TGG ATT GTC
Leu Ser Glu Ala Arg Ser Leu Gly Val Thr Gly Tyr Asp Phe Phe Trp Ile Val 823             832             841             850             859             868
CCC AGC TTG GTC TCT GGG AAC ACG GAG CTC ATC CCA AAA GAG TTT CCA TCG GGA
Pro Ser Leu Val Ser Gly Asn Thr Glu Leu Ile Pro Lys Glu Phe Pro Ser Gly 877             886             895             904             913             922
CTC ATT TCT GTC TCC TAC GAT GAC TGG GAC TAC AGC CTG GAG GCG AGA GTG AGG
Leu Ile Ser Val Ser Tyr Asp Asp Trp Asp Tyr Ser Leu Glu Ala Arg Val Arg 931             940             949             958             967             976
GAC GGC ATT GGC ATC CTA ACC ACC GCT GCA TCT TCT ATG CTG GAG AAG TTC TCC
Asp Gly Ile Gly Ile Leu Thr Thr Ala Ala Ser Ser Met Leu Glu Lys Phe Ser
```

FIG.4B

```
 985         994         1003        1012        1021        1030
TAC ATC CCC GAG GCC AAG GCC AGC TGC TAC GGG CAG ATG GAG AGG CCA GAG GTC
Tyr Ile Pro Glu Ala Lys Ala Ser Cys Tyr Gly Gln MET Glu Arg Pro Glu Val 1039        1048        1057        1066        1075        1084
CCG ATG CAC ACC TTG CAC CCA TTT ATG GTC AAT GTT ACA TGG GAT GGG AAA GAC
Pro MET His Thr Leu His Pro Phe Met Val Asn Val Thr Trp Asp Gly Lys Asp 1093        1102        1111        1120        1129        1138
TTA TCC TTC ACT GAG GAA GGC TAC CAG GTG CAC CCC AGG CTG GTG GTG ATT GTG
Leu Ser Phe Thr Glu Glu Gly Tyr Gln Val His Pro Arg Leu Val Val Ile Val 1147        1156        1165        1174        1183        1192
CTG AAC AAA GAC CGG GAA TGG GAA AAG GTG GCC AAG TGG AAG AAC AAT ACG CTG
Leu Asn Lys Asp Arg Glu Trp Glu Lys Val Ala Lys Trp Lys Asn Asn Thr Leu 1201        1210        1219        1228        1237        1246
AGC CTG AGC CAC GCC GTG TGG CCC AGG TAC AAG TCC TTC TCC GAC TGT GAG CCG
Ser Leu Ser His Ala Val Trp Pro Arg Tyr Lys Ser Phe Ser Asp Cys Glu Pro 1255        1264        1273        1282        1291        1300
GAT GAC AAC CAT CTC AGC ATC GTC ACC CTG GAG GAG GCC CCA TTC GTC ATC GTG
Asp Asp Asn His Leu Ser Ile Val Thr Leu Glu Glu Ala Pro Phe Val Ile Val 1309        1318        1327        1336        1345        1354
GAA GAC ATA GAC CCC CTG ACC GAG ACG TGT GTG AGG AAC ACC GTG CCA TGT CGG
Glu Asp Ile Asp Pro Leu Thr Glu Thr Cys Val Arg Asn Thr Val Pro Cys Arg 1363        1372        1381        1390        1399        1408
AAG TTC GTC AAA ATC AAC AAT TCA ACC AAT GAG GGG ATG AAT GTG AAG AAA TGC
Lys Phe Val Lys Ile Asn Asn Ser Thr Asn Glu Gly MET Asn Val Lys Lys Cys 1417        1426        1435        1444        1453        1462
TGC AAG GGG TTC TGC ATT GAT ATT CTG AAG AAG CTT CCT AGA ACT GTG AAG TTT
Cys Lys Gly Phe Cys Ile Asp Ile Leu Lys Lys Leu Ser Arg Thr Val Lys Phe
```

FIG.4C

```
1471        1480        1489        1498        1507        1516
ACT TAC GAC CTC TAT CTG GTG ACC AAT GGG AAG CAT GGC AAG AAA GGT AAC AAT
Thr Tyr Asp Leu Tyr Leu Val Thr Asn Gly Lys His Gly Lys Lys Val Asn Asn 1525        1534        1543        1552        1561        1570
GTG TGG AAT GGA ATG ATC GGT GAA GTG GTC TAT CAA CGG GCA GTC ATG GCA GTT
Val Trp Asn Gly MET Ile Gly Glu Val Val Tyr Gln Arg Ala Val MET Ala Val 1579        1588        1597        1606        1615        1624
GGC TCG CTC ACC ATC AAT GAG GAA CGT TCT GAA GTG GTG GAC TTC TCT GTG CCC
Gly Ser Leu Thr Ile Asn Glu Glu Arg Ser Glu Val Val Asp Phe Ser Val Pr 1633        1642        1651        1660        1669        1678
TTT GTG GAA ACG GGA ATC AGT GTC ATG GTT TCA AGA AGT AAT GGC ACC GTC TCA
Phe Val Glu Thr Gly Ile Ser Val MET Val Ser Arg Ser Asn Gly Thr Val Ser 1687        1696        1705        1714        1723        1732
CCT TCT GCT TTT CTA GAA CCA TTC AGC GCC TCT GTC TGG GTG ATG ATG TTT GTG
Pro Ser Ala Phe Leu Glu Pro Phe Ser Ala Ser Val Trp Val MET MET Phe Val 1741        1750        1759        1768        1777        1786
ATG CTG CTC ATT GTT TCT GCC ATA GCT GTT TTT GTC TTT GAA TAC TTC AGC CCT
MET Leu Leu Ile Val Ser Ala Ile Ala Val Phe Val Phe Glu Tyr Phe Ser Pro 1795        1804        1813        1822        1831        1840
GTT GGA TAC AAC AGA AAC TTA GCC AAA GGG AAA GCA CCC CAT GGG CCT TCT TTT
Val Gly Tyr Asn Arg Asn Leu Ala Lys Gly Lys Ala Pro His Gly Pro Ser Phe 1849        1858        1867        1876        1885        1894
ACA ATT GGA AAA GCT ATA TGG CTT CTT TGG GGC CTG GTG TTC AAT AAC TCC GTG
Thr Ile Gly Lys Ala Ile Trp Leu Leu Trp Gly Leu Val Phe Asn Asn Ser Val 1903        1912        1921        1930        1939        1948
CCT GTC CAG AAT CCT AAA GGG ACC ACC AGC AAG ATC ATG GTA TCT GTA TGG GCC
Pro Val Gln Asn Pro Lys Gly Thr Thr Ser Lys Ile MET Val Ser Val Trp Ala
```

FIG.4D

```
    1957            1966            1975            1984            1993            2002
TTC TTC GCT     GTC ATA TTC     CTG GCT AGC     TAC ACA GCC     AAT CTG GCT     GCC TTC ATG
Phe Phe Ala     Val Ile Phe     Leu Ala Ser     Tyr Thr Ala     Asn Leu Ala     Ala Phe MET 2011            2020            2029            2038            2047            2056
ATC CAA GAG     GAA TTT GTG     GAC CAA GTG     ACC GGC CTC     AGT GAC AAA     AAG TTT CAG
Ile Gln Glu     Glu Phe Val     Asp Gln Val     Thr Gly Leu     Ser Asp Lys     Lys Phe Gln 2065            2074            2083            2092            2101            2110
AGA CCT CAT     GAC TAT TCC     CCA CCT TTT     CGA TTT GGG     ACA GTG CCT     AAT GGA AGC
Arg Pro His     Asp Tyr Ser     Pro Pro Phe     Arg Phe Gly     Thr Val Pro     Asn Gly Ser 2119            2128            2137            2146            2155            2164
ACG GAG AGA     AAC ATT CGG     AAT AAC TAT     CCC TAC ATG     CAT CAG TAC     ATG ACC AAA
Thr Glu Arg     Asn Ile Arg     Asn Asn Tyr     Pro Tyr MET     His Gln Tyr     MET Thr Lys 2173            2182            2191            2200            2209            2218
TTT AAT CAG     AAA GGA GTA     GAG GAC GCC     TTG GTC AGC     CTG AAA ACG     GGG AAG CTG
Phe Asn Gln     Lys Gly Val     Glu Asp Ala     Leu Val Ser     Leu Lys Thr     Gly Lys Leu 2227            2236            2245            2254            2263            2272
GAC GCT TTC     ATC TAC GAT     GCC GCA GTC     TTG AAT TAC     AAG GCT GGG     AGG GAT GAA
Asp Ala Phe     Ile Tyr Asp     Ala Ala Val     Leu Asn Tyr     Lys Ala Gly     Arg Asp Glu 2281            2290            2299            2308            2317            2326
GGC TGC AAA     CTG GTG ACC     ATC GGG AGT     GGG TAC ATC     TTT GCC ACC     ACC AGT TAT
Gly Cys Lys     Leu Val Thr     Ile Gly Ser     Gly Tyr Ile     Phe Ala Thr     Thr Ser Tyr 2335            2344            2353            2362            2371            2380
GGA ATT GCC     CTT CAG AAA     GGC TCT CCT     TGG AAG AGG     CAG ATC GAC     CTG GCC TTG
Gly Ile Ala     Leu Gln Lys     Gly Ser Pro     Trp Lys Arg     Gln Ile Asp     Leu Ala Leu 2389            2398            2407            2416            2425            2434
CTT CAG TTT     GTG GGT GAT     GGT GAG ATG     GAG GAG CTG     GAG ACC CTG     TGG CTC ACT
Leu Gln Phe     Val Gly Asp     Gly Glu MET     Glu Glu Leu     Glu Thr Leu     Trp Leu Thr
```

FIG.4E

```
     2443           2452           2461           2470           2479           2488
GGG ATC GTC CAC AAC GAG AAG AAC GAG TGT ATG AGC AAC CAG CTG GAC ATT GAC
Gly Ile Val His Asn Glu Lys Asn Glu Cys MET Ser Asn Gln Leu Asp Ile Asp 2497           2506           2515           2524           2533           2542
AAC ATG GCG GGC GTA TTC TAC ATG CTG GCT GCC GCC ATG GCC CTT AGC CTC ATC
Asn MET Ala Gly Val Phe Tyr MET Leu Ala Ala Ala MET Ala Leu Ser Leu Ile 2551           2560           2569           2578           2587           2596
ACC TTC ATC TGG GAG CAC CTC TTC TAC TGG AAG CTG CGC TTC TGT TTC ACG GGC
Thr Phe Ile Trp Glu His Leu Phe Tyr Trp Lys Leu Arg Phe Cys Phe Thr Gly 2605           2614           2623           2632           2641           2650
GTG TGC TCC GAC CGG CCT GGG TTG CTC TTC TCC ATC AGC AGG GGC ATC TAC AGC
Val Cys Ser Asp Arg Pro Gly Leu Leu Phe Ser Ile Ser Arg Gly Ile Tyr Ser 2659           2668           2677           2686           2695           2704
TGC ATT CAT GGA GTG CAC ATT GAA GAA AAG AAG AAG TCT CCA GAC TTC AAT CTG
Cys Ile His Gly Val His Ile Glu Glu Lys Lys Lys Ser Pro Asp Phe Asn Leu 2713           2722           2731           2740           2749           2758
ACG GGA TCC CAG AGC AAC ATG TTA AAA CTC CTC CGG TCA GCC AAA AAC ATT TCC
Thr Gly Ser Gln Ser Asn MET Leu Lys Leu Leu Arg Ser Ala Lys Asn Ile Ser 2767           2776           2785           2794           2803           2812
AGC ATG TCC AAC ATG AAC TCC TCA AGA ATG GAC TCA CCC AAA AGA GCT GCT GAC
Ser MET Ser Asn MET Asn Ser Ser Arg MET Asp Ser Pro Lys Arg Ala Ala Asp 2821           2830           2839           2848           2857           2866
TTC ATC CAA AGA GGT TCC CTC ATC ATG GAC ATG GTT TCA GAT AAG GGG AAT TTG
Phe Ile Gln Arg Gly Ser Leu Ile MET Asp MET Val Ser Asp Lys Gly Asn Leu 2875           2884           2893           2902           2911           2920
ATG TAC TCA GAC AAC AGG TCC TTT CAG GGG AAA GAG AGC ATT TTT GGA GAC AAC
MET Tyr Ser Asp Asn Arg Ser Phe Gln Gly Lys Glu Ser Ile Phe Gly Asp Asn
```

FIG.4F

```
2929            2938            2947            2956            2965            2974
ATG AAC GAA CTC CAA ACA TTT GTG GCC AAC CGG CAG AAG GAT AAC CTC AAT AAC
MET Asn Glu Leu Gln Thr Phe Val Ala Asn Arg Gln Lys Asp Asn Leu Asn Asn 2983            2992            3001            3010            3019            3028
TAT GTA TTC CAG GGA CAA CAT CCT CTT ACT CTC AAT GAG TCC AAC CCT AAC ACG
Tyr Val Phe Gln Gly Gln His Pro Leu Thr Leu Asn Glu Ser Asn Pro Asn Thr 3037            3046            3055            3064            3073            3082
GTG GAG GTG GCC GTG AGC ACA GAA TCC AAA GCG AAC TCT AGA CCC CGG CAG CTG
Val Glu Val Ala Val Ser Thr Glu Ser Lys Ala Asn Ser Arg Pro Arg Gln Leu 3091            3100            3109            3118            3127            3136
TGG AAG AAA TCC GTG GAT TCC ATA CGC CAG GAT TCA CTA TCC CAG AAT CCA GTC
Trp Lys Lys Ser Val Asp Ser Ile Arg Gln Asp Ser Leu Ser Gln Asn Pro Val 3145            3154            3163            3172            3181            3190
TCC CAG AGG GAT GAG GCA ACA GCA GAG AAT AGG ACC CAC TCC CTA AAG AGC CCT
Ser Gln Arg Asp Glu Ala Thr Ala Glu Asn Arg Thr His Ser Leu Lys Ser Pro 3199            3208            3217            3226            3235            3244
AGG TAT CTT CCA GAA GAG ATG GCC CAC TCT GAC ATT TCA GAA ACG TCA AAT CGG
Arg Tyr Leu Pro Glu Glu MET Ala His Ser Asp Ile Ser Glu Thr Ser Asn Arg 3253            3262            3271            3280            3289            3298
GCC ACG TGC CAC AGG GAA CCT GAC AAC AGT AAG AAC CAC AAA ACC AAG GAC AAC
Ala Thr Cys His Arg Glu Pro Asp Asn Ser Lys Asn His Lys Thr Lys Asp Asn 3307            3316            3325            3334            3343            3352
TTT AAA AGG TCA GTG GCC TCC AAA TAC CCC AAG GAC TGT AGT GAG GTC GAG CGC
Phe Lys Arg Ser Val Ala Ser Lys Tyr Pro Lys Asp Cys Ser Glu Val Glu Arg 3361            3370            3379            3388            3397            3406
ACC TAC CTG AAA ACC AAA TCA AGC TCC CCT AGA GAC AAG ATC TAC ACT ATA GAT
Thr Tyr Leu Lys Thr Lys Ser Ser Ser Pro Arg Asp Lys Ile Tyr Thr Ile Asp
```

FIG.4G

```
      3415              3424              3433              3442              3451              3460
GTT GAG AAG GAG CCT GGT TTC CAC TTA GAT CCA CCC CAG TTT GTT GAA AAT GTG
Gly Glu Lys Glu Pro Gly Phe His Leu Asp Pro Pro Gln Phe Val Glu Asn Val 3469              3478              3487              3496              3505              3514
ACC CTG CCC GAG AAC GTG GAC TTC CCG GAC CCC TAC CAG GAT CCC AGT GAA AAC
Thr Leu Pro Glu Asn Val Asp Phe Pro Asp Pro Tyr Gln Asp Pro Ser Glu Asn 3523              3532              3541              3550              3559              3568
TTC CGC AAG GGG GAC TCC ACG CTG CCA ATG AAC CGG AAC CCC TTG CAT AAT GAA
Phe Arg Lys Gly Asp Ser Thr Leu Pro MET Asn Arg Asn Pro Leu His Asn Glu 3577              3586              3595              3604              3613              3622
GAG GGG CTT TCC AAC AAC GAC CAG TAT AAA CTC TAC TCC AAG CAC TTC ACC TTG
Glu Gly Leu Ser Asn Asn Asp Gln Tyr Lys Leu Tyr Ser Lys His Phe Thr Leu 3631              3640              3649              3658              3667              3676
AAA GAC AAG GGT TCC CCG CAC AGT GAG ACC AGC GAG CGA TAC CGG CAG AAC TCC
Lys Asp Lys Gly Ser Pro His Ser Glu Thr Ser Glu Arg Tyr Arg Gln Asn Ser 3685              3694              3703              3712              3721              3730
ACG CAC TGC AGA AGC TGC CTT TCC AAC ATG CCC ACC TAT TCA GGC CAC TTC ACC
Thr His Cys Arg Ser Cys Leu Ser Asn MET Pro Thr Tyr Ser Gly His Phe Thr 3739              3748              3757              3766              3775              3784
ATG AGG TCC CCC TTC AAG TGC GAT GCC TGC CTG CGG ATG GGG AAC CTC TAT GAC
MET Arg Ser Pro Phe Lys Cys Asp Ala Cys Leu Arg MET Gly Asn Leu Tyr Asp 3793              3802              3811              3820              3829              3838
ATC GAT GAA GAC CAG ATG CTT CAG GAG ACA GGT AAC CCA GCC ACC GGG GAG GAG
Ile Asp Glu Asp Gln MET Leu Gln Glu Thr Gly Asn Pro Ala Thr Gly Glu Glu 3847              3856              3865              3874              3883              3892
GTC TAC CAG CAG GAC TGG GCA CAG AAC AAT GCC CTT CAA TTA CAA AAG AAC AAG
Val Tyr Gln Gln Asp Trp Ala Gln Asn Asn Ala Leu Gln Leu Gln Lys Asn Lys
```

FIG.4H

| 3901 | 3910 | 3919 | 3928 | 3937 | 3946 |

CTA AGG ATT AGC CGT CAG CAT TCC TAC GAT AAC ATT GTC GAC AAA CCT AGG GAG
Leu Arg Ile Ser Arg Gln His Ser Tyr Asp Asn Ile Val Asp Lys Pro Arg Glu

| 3955 | 3964 | 3973 | 3892 | 3991 | 4000 |

CTA GAC CTT AGC AGG CCC TCC CGG AGC ATA AGC CTC AAG GAC AGG GAA CGG CTT
Leu Asp Leu Ser Arg Pro Ser Arg Ser Ile Ser Leu Lys Asp Arg Glu Arg Leu

| 4009 | 4018 | 4027 | 4036 | 4045 | 4054 |

CTG GAG GGA AAT TTT TAC GGC AGC CTG TTT AGT GTC CCC TCA AGC AAA CTC TCG
Leu Glu Gly Asn Phe Tyr Gly Ser Leu Phe Ser Val Pro Ser Ser Lys Leu Ser

| 4063 | 4072 | 4081 | 4090 | 4099 | 4108 |

GGG AAA AAA AGC TCC CTT TTC CCC CAA GGT CTG GAG GAC AGC AAG AGG AGC AAG
Gly Lys Lys Ser Ser Leu Phe Pro Gln Gly Leu Glu Asp Ser Lys Arg Ser Lys

| 4117 | 4126 | 4135 | 4144 | 4153 | 4162 |

TCT CTC TTG CCA GAC CAC ACC TCC GAT AAC CCT TTC CTC CAC TCC CAC AGG GAT
Ser Leu Leu Pro Asp His Thr Ser Asp Asn Pro Phe Leu His Ser His Arg Asp

| 4171 | 4180 | 4189 | 4198 | 4207 | 4216 |

GAC CAA CGC TTG GGT ATT GGG AGA TGC CCC TCG GAC CCT TAC AAA CAC TCG TTG
Asp Gln Arg Leu Gly Ile Gly Arg Cys Pro Ser Asp Pro Tyr Lys His Ser Leu

| 4225 | 4234 | 4243 | 4252 | 4261 | 4270 |

CCA TCC CAG GCG GTG AAT GAC AGC TAT CTT CGG TCG TCC TTG AGG TCA ACG GCA
Pro Ser Gln Ala Val Asn Asp Ser Tyr Leu Arg Ser Ser Leu Arg Ser Thr Ala

| 4279 | 4288 | 4297 | 4306 | 4315 | 4324 |

TCG TAC TGT TCC AGG GAC AGT CGG GGC CAC AAT GAT GTG TAT ATT TCG GAG CAT
Ser Tyr Cys Ser Arg Asp Ser Arg Gly His Asn Asp Val Tyr Ile Ser Glu His

| 4333 | 4342 | 4351 | 4360 | 4369 | 4378 |

GTT ATG CCT TAT GCT GCA AAT AAG AAT AAT ATG TAC TCT ACC CCC AGG GTT TTA
Val MET Pro Tyr Ala Ala Asn Lys Asn Asn MET Tyr Ser Thr Pro Arg Val Leu

FIG.41

```
      4387        4396        4405        4414        4423        4432
AAT TCC TGC AGC AAT AGA CGC GTG TAC AAG AAA ATG CCT AGT ATC GAA TCT GAT
Asn Ser Cys Ser Asn Arg Arg Val Tyr Lys Lys MET Pro Ser Ile Glu Ser Asp 4441        4451        4461        4471        4481        4491        4501
      >
GTT TAA AAATCTTCCA TTAATGTTTT ATCTATAGGG AAATATACGT AATGGCCAAT GTTCTGGAGG
Val 4511        4521        4531        4541        4551        4561        4571
GTAAATGTTG AATGTCCAAT AGTGCCCTGC TAAGAGGAAG AAGATGTAGG GAGGTATTTT GTTGTTGTTG 4581        4591        4601        4611        4621        4631        4641
TTGTTGGCTC TTTTGCACAC GGCTTCATGC CATAATCTTC CACTCAAGGA ATCTTGTGAG GTGTGTGCTG 4651        4661        4671        4681        4691        4701        4177
AGCATGGCAG ACACCAGATA GGTGAGTCCT TAACCAAAAA TAACTAACTA CATAAGGGCA AGTCTCCGGG 4721        4731        4741        4751        4761        4771        4781
ACATGCCTAC TGGGTATGTT GCCAATAATG ATGCATTGGA TGCCAATGGT GATGTTATGA TTTCCTATAT 4791        4801        4811        4821        4831        4841        4851
TCCAAATTCC ATTAAGGTCA GCCCACCATG TAATTTTCTC ATCAGAAATG CCTAATGGTT TCTCTAATAC

AGAATAA
```

FIG.4J

HUMAN NMDA R2A RECEPTOR SUBUNIT AND ISOFORMS OF THE HUMAN NMDA-R1 RECEPTOR SUBUNIT AND ENCODING CDNAS

FIELD OF THE INVENTION

The present invention concerns a cell line, and in particular relates to a stable cell line capable of expressing human or animal N-methyl-D-aspartate (NMDA) receptors. The invention also relates to complementary DNAs (cDNAs) encoding novel human NMDA receptor subunits, and concerns in particular the nucleotide and deduced amino acid sequences of the human NMDA R2A receptor subunit, and of various isoforms of the human NMDA R1 receptor subunit.

BACKGROUND

The NMDA receptor is the major excitatory amino acid receptor that mediates glutamate transmission in the central nervous system. This receptor has been implicated in neuronal modulation, including long term potentiation in the hippocampus (Collingridge and Singer, TIPS, 1990, 11, 290). It is consequently believed to play a key role in memory acquisition and learning.

The integral channel of the NMDA receptor allows $ca^{2+}$ to permeate as well as $Na^+$ and $K^+$, and presents at least seven pharmacologically distinct sites. These include a glutamate binding site, a glycine binding site, a polyamine site, a dizocilpine binding site, a voltage dependent $Mg^{2+}$ site, a $Zn^{2+}$ binding site (Wong and Kemp, Ann. Rev. Pharmacol. Toxicol., 1991, 31, 401) and an ifenprodil binding site (Carter et al., J. Pharmacol. Exy. Ther., 1988, 247, 1222).

The development of potent and selective NMDA receptor antagonists which penetrate into the brain has received considerable attention of late as an attractive strategy for treating and/or preventing conditions which are believed to arise from over-stimulation of neurotransmitter release by excitatory amino acids. Such conditions notably include neurodegenerative disorders arising as a consequence of such pathological conditions as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Amyotrophic Lateral Sclerosis, Parkinson's disease, Olivo-ponto-cerebellar atrophy, anoxia such as from drowning, spinal cord and head injury, and poisoning by exogenous and endogenous NMDA receptor agonists and neurotoxins, including environmental neurotoxins.

NMDA receptor antagonists may also be useful as anticonvulsant and antiemetic agents, as well as being of value in the prevention or reduction of dependence on dependence-inducing agents such as narcotics.

NMDA receptor antagonists have recently been shown to possess analgesic (see, for example, Dickenson and Aydar, Neuroscience Lett., 1991, 121, 263; Murray et al., Pain, 1991, 44, 179; and Woolf and Thompson, Pain, 1991, 44, 293) and anxiolytic (see, for example, U.S. Pat. No. 5,145, 866; and Kehne et al., Eur. J. Pharmacol., 1991, 193, 283) effects, and such compounds may accordingly be useful in the management of pain, depression and anxiety.

Compounds possessing functional antagonist properties for the NMDA receptor complex are stated in WO-A-91/19493 to be effective in the treatment of mood disorders, including major depression, bipolar disorder, dysthymia and seasonal affective disorder (cf. also Trullas and Skolnick, Eur. J. Pharmacol., 1990, 185, 1). Such compounds may consequently be of benefit in the treatment and/or prevention of those disorders.

The association of NMDA receptor antagonists with regulation of the dopaminergic system has recently been reported (see, for example, Werling et al., J. Pharmacol. Exp. Ther., 1990, 255, 40; Graham et al., Life Sciences, 1990, 47, PL-41; Hutson et al., Br. J. Pharmacol., 1991, 103, 2037; and Turski et al., Nature (London), 1991, 349, 414). This suggests that such compounds may thus be of assistance in the prevention and/or treatment of disorders of the dopaminergic system such as schizophrenia and Parkinson's disease.

It has also been reported recently (see Lauritzen et al., Journal of Cerebral Blood Flow and Metabolism, 1991, vol. 11, suppl. 2, Abstract XV-4) that NMDA receptor antagonists block cortical spreading depression (CSD), which may thus be of clinical importance since CSD is a possible mechanism of migraine. The class of substituted 2-amino-4-phosphonomethylalk-3-ene carboxylic acids and esters described in EP-A0420806, which are stated to be selective NMDA antagonists, are alleged thereby to be of potential utility in the treatment of inter alia migraine.

Excitatory amino acid receptor antagonists, including inter alia antagonists of NMDA receptors, are alleged in EP-A-0432994 to be of use in suppressing emesis.

Recent reports in the literature have also suggested a link between the neurotoxicity of certain viruses and the deleterious effects of these viruses on an organism caused by the potentiation of neurotransmission via excitatory amino acid receptors. Antagonists of NMDA receptors may therefore be effective in controlling the manifestations of neuroviral diseases such as measles, rabies, tetanus (cf. Bagetta et al., Br. J. Pharmacol., 1990, 101, 776) and AIDS (cf. Lipton et al., Society for Neuroscience Abstracts, 1990, 16, 128.11).

NMDA antagonists have, moreover, been shown to have an effect on the neuroendocrine system (see, for example, van den Pol et al., Science, 1990, 250, 1276; and Urbanski, Endocrinology, 1990, 127, 2223), and such compounds may therefore also be effective in the control of seasonal breeding in mammals.

A cDNA, encoding a subunit of the rat NMDA receptor and designated NMDA R1, has been cloned by expression cloning (Moriyoshi et al., Nature (London), 1991, 354, 31). When expressed in Xenopus oocytes, this cDNA exhibits the electrophysiological and pharmacological properties expected of an authentic NMDA receptor, although the levels of expression are extremely low. More recently, the existence of several discrete isoforms of the rat NMDA R1 receptor subunit, generated by alternative RNA splicing, has been reported (Sugihara et al., BBRC, 1992, 185, 826). Using both low stringency hybridization and polymerase chain reaction methodologies, four additional rodent NMDA receptor subunit cDNAs have been cloned: ε1 or NMDA R2A; ε2 or NMDA R2B; ε3 or NMDA R2C; and ε4 or NMDA R2D (see Monyer et al., Science, 1992, 256, 1217; Kutsuwada et al., Nature (London), 1992, 358, 36; Ikeda et al., FEBS Lett., 1992, 313, 34; and Ishii et al., J. Biol. Chem., 1993, 268, 2836). Co-expression in Xenopus oocytes or transiently transfected cells of the NMDA R1 subunit, with any one of the R2A, R2B, R2C or R2D subunits referred to above, gives rise to a more robust NMDA receptor than that constituted by the NMDA R1 subunit alone (Monyer et al., Science, 1992, 256, 1217). Moreover, these four resulting putative NMDA receptors (R1/R2A; R1/R2B; R1/R2C; and R1/R2D) are observed to be pharmacologically and electrophysiologically distinguishable. These data support the hypothesis that a family of NMDA receptor subtypes with distinct pharmacological profiles may exist in the brain through combination of different subunits.

Any of a variety of procedures may be used to molecularly clone human NMDA receptor cDNA. These methods include, but are not limited to, direct functional expression of the human NMDA receptor cDNAs following the construction of a human NMDA receptor containing cDNA library in an appropriate expression vector system. Another method is to screen a human NMDA receptor containing cDNA library constructed in a bacteriophage or plasmid shuttle vector with a labelled oligonucleotide probe designed from the amino acid sequence of the purified NMDA receptor protein or from the DNA sequence of known NMDA receptor cDNAs. The preferred method consists of screening a human NMDA receptor containing cDNA library constructed in a bacteriophage or plasmid shuttle vector with a $^{32}$P-labelled cDNA oligonucleotide-primed fragment of rodent NMDA receptor subunit cDNA. The preferred human cDNA library is a commercially available human hippocampal cDNA library.

It is readily apparent to those skilled in the art that other types of libraries, as well as libraries constructed from other brain regions, may be useful for isolating DNA encoding the human NMDA receptor. Other types of libraries include, but are not limited to, cDNA libraries derived from other tissues, cells or cell lines other than human hippocampal cells, and genomic DNA libraries.

Preparation of cDNA libraries can be performed by standard techniques well known in the art. Well known cDNA library construction techniques can be found, for example, in Maniatis, T., Fritsch, E. F., Sambrook, J., *Molecular Cloning: A Laboratory Manual* (Cold Spring Harbor Press, New York, 2nd edition, 1989).

It is also readily apparent to those skilled in the art that DNA encoding the human NMDA receptor may also be isolated from a suitable genomic DNA library.

Construction of genomic DNA libraries can be performed by standard techniques well known in the art. Well known genomic DNA library construction techiques can be found in Maniatis et al., supra.

BRIEF DESCRIPTION OF THE DRAWINGS

FIGS. 2A–2E shows the nucleotide sequence (SEQ ID NO:13) of the R1e isoform and a translation of the encoded amino acids (SEQ ID NO:2).

FIGS. 3A–3B depicts the alternative carboxy terminal sequences of the cDNAs encoding the R1a (2613–2854 of SEQ ID NO:11), R1d (2613–2807 of SEQ ID NO:12) and R1e (2613–2694 of SEQ ID NO:13) isoforms of the human NMDA R1 receptor subtypes and translations of the encoded amino acids. Deletion 1 (SEQ ID NO:3), deletion 2 (SEQ ID NO:5) and the alternate sequence (SEQ ID NO:7) are also shown with translations of the encoded amino acids.

FIGS. 4A–4J shows the nucleotide sequence (SEQ ID NO:9) of the cDNA encoding the human NMDA R2A receptor subunit and a translation of the encoded amino acids.

DETAILED DESCRIPTION

Using the preferred method, cDNA clones encoding the human NMDA receptor were isolated by cDNA library screening. $^{32}$P-radiolabelled fragments of rodent NMDA receptor NMDA R1 and NMDA R2A subunit cDNAs served as probes for the isolation of human NMDA receptor cDNA from a commercially available cDNA library derived from human hippocampal tissue.

For the NMDA R1 subunit, several positively hybridising clones were detected using the rodent NMDA R1 subunit cDNA probe. The longest of these cDNA clones, which was homologous to the published NMDA R1e isoform (Sugihara et al., *BBRC*, 1992, 185, 826), lacked approximately 300 base pairs of the 5' end of the coding region. The missing sequence could be restored by conventional techniques, which essentially involved screening the same hippocampal cDNA library with an EcoRI-SmaI fragment encoding the last 300 nucleotides of the 5' end of the truncated NMDA R1e clone. A cDNA clone containing the missing sequence could be isolated and engineered by standard methods onto the truncated NMDA R1e cDNA at the internal SmaI site in order to generate a full-length NMDA R1e cDNA, as described in accompanying Example 1.

Analogous techniques applied to other positive clones isolated from the human hippocampal cDNA library have yielded cDNAs encoding isoforms of the human NMDA R1 receptor subunit corresponding to the published rat NMDA R1a and NMDA R1d isoforms (Sugihara et al., sudra).

For the NMDA R2A subunit, several hybridising clones were detected using the rodent NMDA R2A subunit cDNA probe. As with the situation encountered in connection with the R1 subunit as described above, none of these cDNAs obtained from the human hippocampal cDNA library encoded the complete human NMDA R2A deduced amino acid sequence. For this reason, a full-length cDNA was constructed from overlapping truncated cDNAs, as described in accompanying Example 2.

Figure 1:
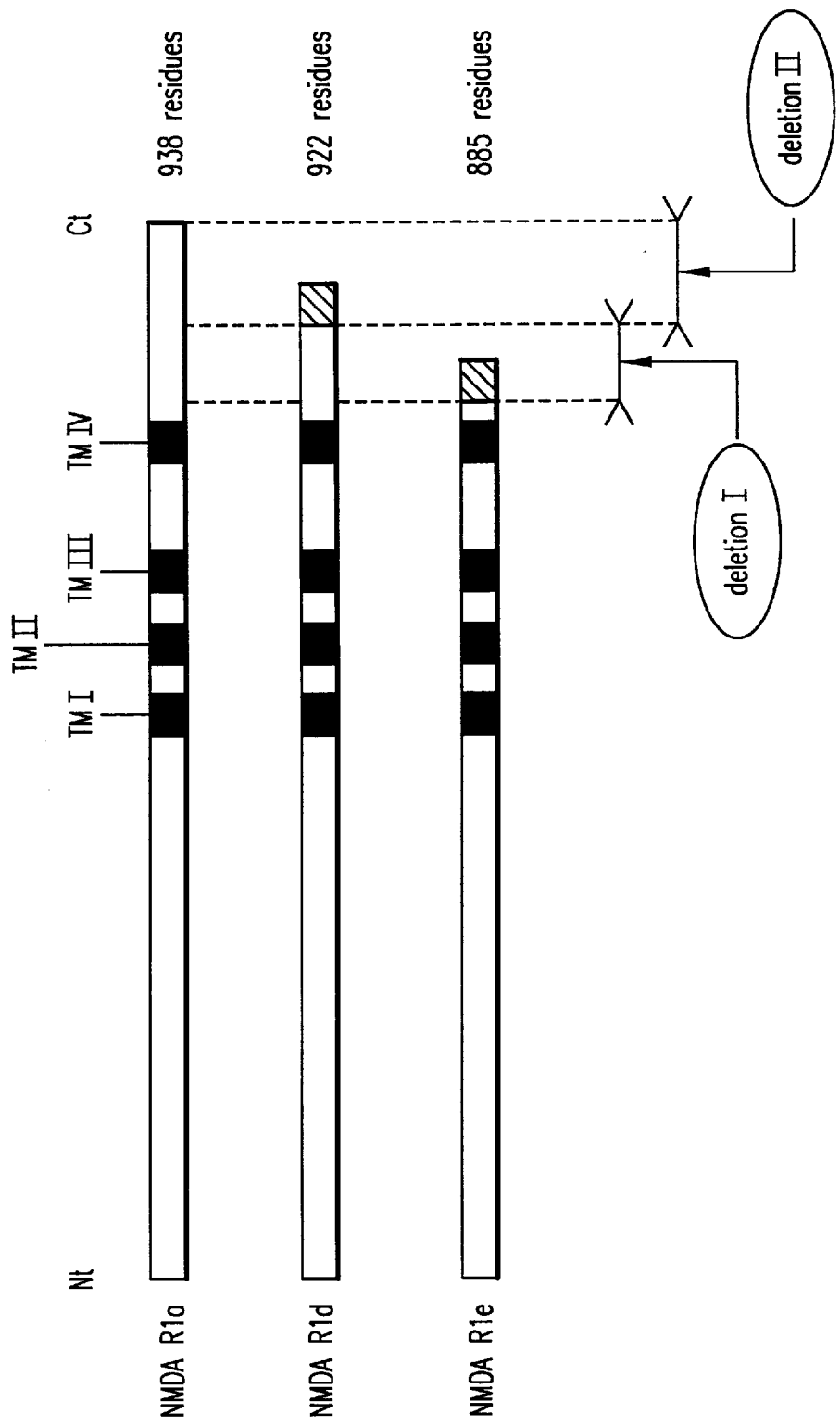
FIG. 1 shows a schematic comparison of NMDAR1-a, NMDAR1-d, NMDAR1-e.

FIG. 1 depicts the schematic structures of the R1a, R1d and R1e isoforms of the human NMDA R1 receptor subtype. Four putative transmembrane segments (TMI-IV) are represented by solid boxes. R1d has a deletion (deletion II) at the region corresponding to nucleotide residues no. 2701–3056 of the R1a cDNA. This deletion results in the generation of a new 22 amino acid carboxyl-terminal (Ct) sequence that follows amino acid residue 900 of the R1a sequence. R1e has a further deletion (deletion I) and accordingly lacks the sequences of both deletions I and II, thus possessing a structure with the new 22 amino acid carboxyl-terminal sequence linked to the R1a sequence at position 863. This 22 amino acid carboxyl-terminal sequence, created by alternative splicing, is indicated in FIG. 1 by hatched boxes.

The sequence for the full-length cDNA encoding the R1e isoform of the human NMDA receptor is shown in FIGS. 2A to 2E (SEQ ID NO:13). The deduced amino acid sequence (SEQ ID NO:2) is shown alongside the cDNA sequence in FIGS. 2A to 2E. The positions of the four putative transmembrane segments (TM1-4) and of the predicted signal peptide (SP) are indicated in FIGS. 2A to 2E by solid lines.

FIG. 3 depicts the alternative carboxy-terminal sequences of the cDNAs encoding the R1a, R1d and R1e isoforms of the human NMDA R1 receptor subtype. The nucleotide and deduced amino acid sequences are indicated in FIG. 3 for each isoform. Indicated amino acid position 863 and nucleotide position 2589 relate to the corresponding positions in the sequence of the R1e isoform depicted in FIGS. 2A to 2E. The nucleotide and deduced amino acid sequences of deletion I (37 amino acids) and deletion II (38 amino acids) are indicated in FIG. 3. The R1d and R1e isoforms are generated from the R1a isoform by a combination of deletion I and deletions I+II respectively, followed by the addition of the alternative 22 amino acid carboxy-terminal sequence represented by the hatched boxes in FIG. 1, the nucleotide and deduced amino acid sequences of which are indicated in FIG. 3. The untranslated domains are represented in lower case lettering.

The complete nucleotide and deduced amino acid sequences of the cDNA encoding the human NMDA R2A receptor subunit are shown in FIGS. 4A to 4J. The cDNA is 4858 bases long. The open reading frame is between bases 47 and 4438. Bases 1–46 are 5' untranslated sequence, and bases 4439–4858 are 3' untranslated sequence. The deduced amino acid sequence is 1464 residues long and has 81 differences from the published rat NMDA R2A sequence (Monyer et al., *Science,* 1992, 256, 1217).

The cloned human NMDA receptor cDNA obtained through the methods described above may be recombinantly expressed by molecular cloning into an expression vector containing a suitable promoter and other appropriate transcription regulatory elements, and then transferring the expression vector into prokaryotic or eukaryotic host cells to produce a recombinant NMDA receptor. Techniques for such manipulations are fully described in Maniatis et al., supra, and are well known in the art.

DNA encoding the NMDA receptor cloned into an expression vector may then be transferred to a recombinant host cell for expression. Recombinant host cells may be prokaryotic or eukaryotic, including but not limited to bacteria, yeast, mammalian cells (including but not limited to cell lines of human, bovine, porcine, monkey and rodent origin), and insect cells (including but not limited to drosophila derived cell lines). Cell lines derived from mammalian species which may be suitable and which are commercially available include, but are not limited to, L-M (ATCC CCL 1), HEK293 (ATCC CCL 1555), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

The expression vector may be introduced into host cells via any one of a number of techniques including but not limited to transformation, transfection, protoplast fusion, and electroporation. The expression vector-containing cells are clonally propagated and individually analyzed to determine whether they produce NMDA receptor protein. Identification of NMDA receptor expressing host cell clones may be done by several means, including but not limited to immunological reactivity with anti-NMDA receptor antibodies, and the presence of host cell-associated NMDA receptor activity.

Expression of NMDA receptor DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes.

To determine the NMDA receptor cDNA sequence(s) that yield(s) optimal levels of binding activity and/or NMDA receptor protein, NMDA receptor cDNA molecules including but not limited to the following can be constructed: the full-length open reading frame of the human NMDA receptor cDNA depicted in FIGS. 2A to 2E or FIGS. 4A to 4J and constructs containing portions of the cDNA encoding biologically active human NMDA receptor protein. All constructs can be designed to contain none, all, or portions of the 5' and 3' untranslated region of human NMDA receptor cDNA. NMDA receptor activity and levels of protein expression can be determined following the introduction, both singly and in combination, of these constructs into appropriate host cells. Following determination of the NMDA receptor cDNA cassette which yields optimal expression, this cDNA construct may be transferred to a variety of expression host cells, including but not limited to mammalian cells, baculovirus-infected insect cells, *E. coli,* and the yeast *S. cerevisiae.*

Expression of the human NMDA receptor in a recombinant host cell affords NMDA receptor protein in active form. Several purification procedures are available and suitable for use. Recombinant NMDA receptor may suitably be purified from cell lysates and extracts, or from conditioned culture medium, by various combinations of, or individual application of, salt fractionation, ion exchange chromatography, size exclusion chromatography, hydroxylapatite adsorption chromatography and hydrophobic interaction chromatography.

In addition, recombinant human NMDA receptor can be separated from other cellular proteins by use of an immunoaffinity column made with monoclonal or polyclonal antibodies specific for the NMDA receptor, or polypeptide fragments thereof. The preparation and purification of monoclonal or polyclonal antibodies specific for the NMDA receptor or polypeptide fragments thereof can be accomplished by conventional techniques well known in the art. Typical procedures include those described, for example, by Maniatis et al., in *Molecular Cloning, A Laboratory manual,* Cold Harbor Press, New York, 2nd edition, 1989, Chapter 18.

The present invention is concerned with the production of permanently transfected cells containing the NMDA receptor, which will be useful for screening for drugs which act on this receptor. The NMDA receptor has previously been expressed in Xenopus oocytes (Ishii et al., *J. Biol. Chem.,* 1993, 268, 2836) and in transiently transfected mammalian cells (Monyer et al., *Science,* 1992, 256, 1217). However, both of those systems involve transient expression and are unsuitable for screening purposes.

We have now achieved the stable expression of the receptor.

Accordingly, the present invention provides a stably co-transfected eukaryotic cell line capable of expressing an NMDA receptor, which receptor comprises at least one R1 subunit isoform, or at least one R1 subunit isoform and one or two R2 subunits.

This has been achieved by co-transfecting cells with expression vectors, each harbouring cDNAs encoding for at least one R1 subunit isoform, or for at least one R1 subunit isoform and one or two R2 subunits respectively. In a further aspect, therefore, the present invention provides a process for the preparation of a eukaryotic cell line capable of expressing an NMDA receptor, which comprises stably co-transfecting a eukaryotic host cell with one or more expression vectors, at least one such vector harbouring the cDNA sequence encoding for an NMDA R1 receptor subunit isoform (referred to in the art as the "key subunit"), and optionally other such vectors harbouring the cDNA sequences encoding for one or two different NMDA R2 receptor subunits. The stable cell line which is established expresses an R1 or an R1+R2 NMDA receptor respectively. Each receptor thereby expressed, comprising a unique combination of at least one R1 subunit isoform, or at least one R1 subunit isoform and one or two R2 subunits, will be referred to hereinafter as an NMDA receptor "subunit combination". Pharmacological and electrophysiological data confirm that the recombinant R1 or R1+R2 receptors expressed by the cells of the present invention have the properties expected of a native NMDA receptor.

As indicated above, expression of the NMDA receptor may be accomplished by a variety of different promoter-expression systems in a variety of different host cells. The eukaryotic host cells suitably include yeast, insect and mammalian cells. Preferably the eukaryotic cells which can provide the host for the expression of the receptor are mammalian cells. Suitable host cells include rodent fibroblast lines, for example mouse Ltk$^-$, Chinese hamster ovary (CHO) and baby hamster kidney (BHK); HeLa; and HEK293 cells. It is necessary to incorporate at least one R1 subunit isoform, or at least one R1 subunit isoform and one or two R2 subunits, into the cell line in order to produce the required receptor, referred to as R1 or R1+R2 respectively. Within this limitation, the choice of receptor subunit combination is made according to the type of activity or selectivity which is being screened for.

In order to employ this invention most effectively for screening purposes, it is preferable to build up a library of cell lines, each with a different combination of subunits. Typically a library of 11 cell line types is convenient for this purpose. Preferred subunit combinations include: R1, R1+R2A, R1+R2B, R1+R2C, R1+R2D, R1+R2A+R2B, R1+R2A+R2C, R1+R2A+R2D, R1+R2B+R2C, R1+R2B+R2D and R1+R2C+R2D. The nomenclature 'R1' signifies any one of the seven reported isoforms of the NMDA R1 subunit (Sugihara et al., *BBRC*, 1990, 185, 826): R1a, R1b, R1c, R1d, R1e, R1f and R1g. A particular subunit combination is R1a+R2A.

In a particular embodiment, the present invention provides a stably co-transfected eukaryotic cell line capable of expressing a human NMDA receptor comprising the R1a subunit isoform.

In a further embodiment, the present invention provides a stably co-transfected eukaryotic cell line capable of expressing a human NMDA receptor comprising the R1a+R2A subunit combination.

As indicated above, the DNAs for the receptor subunits can be obtained from known sources, and are generally obtained as specific nucleotide sequences harboured by a standard cloning vector such as those described, for example, by Maniatis et al., supra. Preferably the cDNA sequences are derived from the human gene. However, for screening purposes, cDNAs from other species are also suitable, such as bovine or rat DNA. Known sources of NMDA receptor subunit cDNAs are as follows:

R1 isoforms (rat): Sugihara et al., *BBRC*, 1992, 185, 826. Durand et al., *PNAS*, 1992, 89, 9359. Hollmann et al., *Neuron*, 1993, 10, 943.
R2A, R2B, R2C, R2D (rat): Ishii et al., *J. Biol. Chem.*, 1993, 268, 2836.
R2A, R2B, R2C (rat): Monyer et al., *Science*, 1992, 256, 1217.
R1e (human): Planells-Cases, *PNAS*, 1993, 90, 5057.
R1a (human): Karp et al., *J. Biol. Chem.*, 1993, 268, 3728.
R1a=($\zeta$1, R2A=$\epsilon$1, R2B=$\epsilon$2, R2C=$\epsilon$3 (mouse): Kutsuwada et al., *Nature*, 1992, 358, 36.

In another aspect, the invention provides a recombinant expression vector comprising the nucleotide sequence of an NMDA receptor subunit together with additional sequences capable of directing the synthesis of the said NMDA receptor subunit in cultures of stably co-transfected eukaryotic cells.

The term "expression vectors" as used herein refers to DNA sequences that are required for the transcription of cloned copies of recombinant DNA sequences or genes and the translation of their mRNAs in an appropriate host. Such vectors can be used to express eukaryotic genes in a variety of hosts such as bacteria, blue-green algae, yeast cells, insect cells, plant cells and animal cells. Specifically designed vectors allow the shuttling of DNA between bacteria-yeast, bacteria-plant or bacteria-animal cells. An appropriately constructed expression vector should contain an origin of replication for autonomous replication in host cells; selectable markers; a limited number of useful restriction enzyme sites; a potential for high copy number; and strong promoters. A promoter is defined as a DNA sequence that directs RNA polymerase to bind to DNA and to initiate RNA synthesis. A strong promoter is one which causes mRNAs to be initiated at high frequency. Expression vectors may include, but are not limited to, cloning vectors, modified cloning vectors, specifically designed plasmids or viruses.

The term "cloning vector" as used herein refers to a DNA molecule, usually a small plasmid or bacteriophage DNA capable of self-replication in a host organism, and used to introduce a fragment of foreign DNA into a host cell. The foreign DNA combined with the vector DNA constitutes a recombinant DNA molecule which is derived from recombinant technology. Cloning vectors may include plasmids, bacteriophages, viruses and cosmids.

A variety of mammalian expression vectors may be used to express recombinant NMDA receptor in mammalian cells. Commercially available mammalian expression vectors which may be suitable for recombinant NMDA receptor expression include, but are not limited to, pCDNAneo (Invitrogen), pCDNAI-Amp (Invitrogen), pCDM8 (Invitrogen), pMSGneo (*Proc. Natl. Acad. Sci. USA*, 1992, 89, 6378), pMC1neo (Stratagene), pXT1 (Stratagene), pSG5 (Stratagene), EBO-pSV2-neo (ATCC 37593), pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and gZD35 (ATCC 37565).

The recombinant expression vector in accordance with the invention may be prepared by inserting the nucleotide sequence of the chosen NMDA subunit into a suitable precursor expression vector (hereinafter referred to as the "precursor vector") using conventional recombinant DNA methodology known from the art. The precursor vector may be obtained commercially, or constructed by standard techniques from known expression vectors. The precursor vector suitably contains a selection marker, typically an antibiotic resistance gene, such as the neomycin or ampicillin resistance gene. The precursor vector preferably contains a neomycin resistance gene, adjacent the SV40 early splicing and polyadenylation region; an ampicillin resistance gene; and an origin of replication, e.g. pBR322 ori. The vector also preferably contains an inducible promoter, such as MMTV-LTR (inducible with dexamethasone) or metallothionin (inducible with zinc), so that transcription can be controlled in the cell line of this invention. This reduces or avoids any problem of toxicity in the cells because of the ion channel intrinsic to the NMDA receptor.

One suitable precursor vector is pMAMneo, available from Clontech Laboratories Inc. (Lee et al., *Nature*, 1981, 294, 228; and Sardet et al., *Cell*, 1989, 56, 271). Alternatively the precursor vector pMSGneo can be constructed from the vectors pMSG and pSV2neo as described in Example 3 herein.

The recombinant expression vector of the present invention is then produced by cloning the NMDA receptor subunit cDNA into the above precursor vector. The required receptor subunit cDNA is subcloned from the vector in which it is harboured, and ligated into a restriction enzyme site in the polylinker of the precursor vector, for example pMAMneo or pMSGneo, by standard cloning methodology known from the art, and in particular by techniques analogous to those described in Example 3, step (b) herein.

Figure 5:
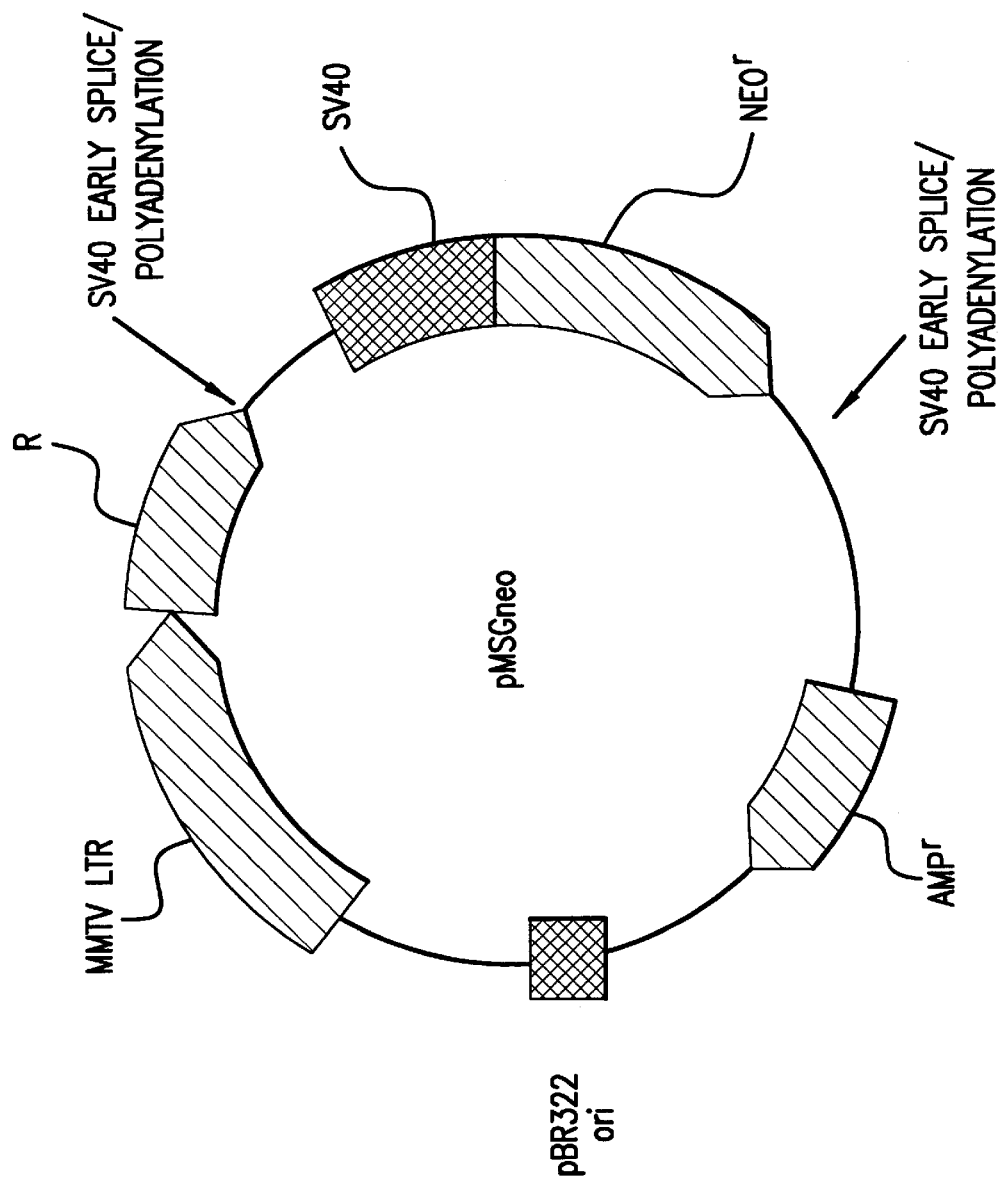
FIG. 5 is a schematic representation of cloning vector pMSGneo in which "R" represents the nucleotide sequence of a chosen R1 or R2 subunit of the NMDA receptor, and the remainder of the expression vector depicted therein is derived from the precursor vector pMSGneo and constructed as described in Example 3, steps (a) and (b).

One suitable expression vector of the present invention is illustrated in FIG. 5 of the accompanying drawings, in which R represents the nucleotide sequence of a chosen R1 or R2 subunit of the NMDA receptor, and the remainder of the expression vector depicted therein is derived from the precursor vector pMSGneo and constructed as described in accompanying Example 3, steps (a) and (b).

For each cell line of the present invention, one or more such vectors will be necessary. At least one such vector will contain the cDNA sequence encoding for an R1 subunit isoform. Vectors containing the cDNA sequences encoding for one or two different R2 subunits may also be utilised.

Cells are then co-transfected with the desired combination of one or more, typically one, two or three, expression vectors. There are several commonly used techniques for transfection of eukaryotic cells in vitro. Calcium phosphate precipitation of DNA is most commonly used (Bachetti et al., *Proc. Natl. Acad. Sci. USA*, 1977, 74, 1590–1594; Maitland et al., *Cell*, 1977, 14, 133–141), and represents a favoured technique in the context of the present invention.

A small percentage of the host cells takes up the recombinant DNA. In a small percentage of those, the DNA will integrate into the host cell chromosome. Because the neomycin resistance gene will have been incorporated into these host cells, they can be selected by isolating the individual clones which will grow in the presence of neomycin. Each such clone is then tested to identify those which will produce the receptor. This is achieved by inducing the production, for example with dexamethasone, and then detecting the presence of receptor by means of radioligand binding.

In a further aspect, the present invention provides protein preparations of NMDA receptor subunit combinations, especially human NMDA receptor subunit combinations, derived from cultures of stably transfected eukaryotic cells. The invention also provides preparations of membranes containing subunit combinations of the NMDA receptor, especially human NMDA receptor subunit combinations, derived from cultures of stably transfected eukaryotic cells. In particular, the protein preparations and membrane preparations according to the invention will suitably contain the R1, R1+R2A, R1+R2B, R1+R2C, R1+R2D, R1+R2A+R2B, R1+R2A+R2C, R1+R2A+R2D, R1+R2B+R2C, R1+R2B+R2D or R1+R2C+R2D subunit combinations of the human NMDA receptor, wherein the nomenclature 'R1' signifies any one of the several isoforms of the R1 subunit as described above. A preferred subunit combination is the R1a+R2A subunit combination. In an especially preferred embodiment, the invention provides cell membranes containing a human NMDA receptor consisting of the R1a+R2A subunit combination isolated from stably transfected mouse Ltk⁻ fibroblast cells.

The cell line, and the membrane preparations therefrom, according to the present invention have utility in screening and design of drugs which act upon the NMDA receptor. The present invention accordingly provides the use of the cell line described above, of membrane preparations derived therefrom, and of the cloned human NMDA receptor as described herein, in screening for and designing medicaments which interact selectively with the NMDA receptor. Of particular interest in this context are molecules capable of interacting selectively with NMDA receptors made up of varying subunit combinations. As will be readily apparent, the cell line in accordance with the present invention, and the membrane preparations derived therefrom, provide ideal systems for the study of structure, pharmacology and function of the various NMDA receptor subtypes.

This invention provides an antisense oligonucleotide having a sequence capable of binding specifically with any sequences of an MRNA molecule which encodes the human NMDA receptor, so as to prevent translation of the mRNA molecule. The antisense oligonucleotide may have a sequence capable of binding specifically with any sequences of the cDNA molecule whose sequence is shown in, for example, FIG. 3 or FIGS. 4A–4J. A particular example of an antisense oligonucleotide is an antisense oligonucleotide comprising chemical analogues of nucleotides.

This invention provides a transgenic nonhuman mammal expressing DNA encoding the human NMDA receptor. This invention also provides a transgenic nonhuman mammal, so mutated as to be incapable of normal receptor activity, and not expressing the native NMDA receptor, which mammal is nonetheless capable of expressing DNA encoding the human NMDA receptor. This invention further provides a transgenic nonhuman mammal whose genome comprises antisense DNA complementary to DNA encoding the native NMDA receptor, so placed as to be transcribed into antisense mRNA which is complementary to mRNA encoding the receptor and which hybridizes to MRNA encoding the receptor thereby reducing its translation. The DNA may additionally comprise an inducible promoter or additionally comprise tissue specific regulatory elements, so that expression can be induced, or restricted to specific cell types. Examples of DNA are DNA or cDNA molecules having a coding sequence substantially the same as the coding sequence shown in, for example, FIG. 3 or FIGS. 4A to 4J. An example of a transgenic animal is a transgenic mouse. Examples of tissue specificity-determining regions are the metallothionein promoter (Low et al., *Science*, 1986, 231, 1002–1004) and the L7 promoter (Oberdick et al., *Science*, 1990, 248, 223–226).

The following non-limiting Examples illustrate the present invention.

EXAMPLE 1

Isolation of cDNAs Encoding Three Different Isoforms of the Human NMDA R1 Receptor Subunit 1. Methods Oligonucleotide primers derived from the published rat NMDA R1 receptor sequence (Moriyoshi et al., *Nature (London)*, 1991, 354, 31–37) [$0_1$: 5' GAC/CCC/AGG/CTC/

AGA/ATT/CCC/TCA/GAC/AAG3' SEQ ID NO:14 and 30$_2$: 5' CAC/CAG/GAA/GAA/GTC/TGC/CAT/GTT/CTC/A3' SEQ ID NO:15] were used in the polymerase chain reaction (PCR) to isolate a 420 bp cDNA encoding the putative large cytoplasmic loop of the human NMDA R1 receptor subtype. A human hippocampal cDNA library was screened at low stringency (55° C. in 5×SSPE, 5×Denhardt's solution, 0.1% SDS, 100 µg/ml salmon sperm DNA) using this partial PCR cDNA as a [$^{32}$P]-labelled probe containing 0.5×10$^6$ cpm/ml. Twenty positive clones encoding putative NMDA receptors were isolated. The longest clone, homologous to the published NMDA R1e, 0.6 kb long, was lacking approximately 300 bp of the 5' end of the coding region. This missing sequence was obtained by screening the same human hippocampal cDNA library with an EcoR1-SmaI fragment encoding the last 300 nucleotides of the 5' end of the truncated NMDA R1e clone. A cDNA clone containing the missing sequence was isolated and engineered onto the truncated NMDA R1e cDNA at the internal SmaI site in order to generate a full length NMDA R1e cDNA. This full length human NMDA R1e clone contains a 2.8 kb coding sequence flanked by 0.05 kb and 0.6 kb of the 5' and the 3' untranslated regions respectively.

2. Results

The sequence of the human NMDA R1e cDNA (FIG. 2A to 2E) is homologous (98.6% of homology) with the published rat NMDA R1e cDNA (Sugihara et al., *BBRC*, 1992, 185, 826–832). The amino acid sequence of the C-terminal domain of this NMDA R1e subunit differs from the original published rat NMDA R1a subunit (Moriyoshi et al., *Nature (London)*, 1991, 354, 31–37). Among the twenty positive clones isolated from a human hippocampal cDNA library, screened with the 420 bp long PCR fragment, two other clones have revealed a sequence homologous to the NMDA R1e; they are the human version of the published rat NMDA R1a and NMDA R1d, respectively (Sugihara et al., *BBRC*, 1992, 185, 826–832). FIG. 1 shows the schematic structures of the three human NMDA R1a, R1d and R1e isoforms, on the basis of the structural comparison with the original NMDA R1 (now referred to as R1a). R1d has a deletion (deletion II, whose nucleotide and deduced amino acid sequences are shown in FIG. 3) at the region corresponding to nucleotide residues no. 2701–3056 of the R1a cDNA. This deletion results in the generation of a new 22 amino acid carboxyl-terminal sequence that follows amino acid residue 900 of the R1a sequence. The nucleotide and deduced amino acid sequences of this new 22 amino acid sequence are depicted in FIG. 3. R1e has a further deletion (deletion I, whose nucleotide and deduced amino acid sequences are shown in FIG. 3) and accordingly lacks the sequences of both deletions I and II, thus possessing a structure with the new 22 amino acid carboxyl-terminal sequence (cf. FIG. 3) linked to the R1a sequence at position 863.

EXAMPLE 2

Isolation of cDNAs Encoding the Human NMDA R2A Subunit

Oligonucleotide primers derived from the published rat NMDA R2A cDNA sequence (Monyer et al., *Science*, 1992, 256, 1217) were used in the polymerase chain reaction (PCR) to generate N-terminal and C-terminal cDNA probes. Primers for N-terminal probe (encoding residues Leu16-Met74) were (SEQ ID NO:16) 5'TGCCGGGAATTCTG-GTCTGGCGCGATCCGG3' and (SEQ ID NO:17) 5'GGGT-CAAGCTTTTCATCAATAACGCCAC3'. Primers for the C-terminal probe (encoding residues Leu898-Gln1209) were SEQ ID NO:18 5'TGCTAAGATTCTTCGGT-CAGCTAAAAAC3' SEQ ID NO:19 and 5'AATGT-GAAGCTTTCTGCCGGTATCGATCAC3'. The sense oligonucleotide (the first of each pair) had an EcoRI restriction enzyme site incorporated into it, while the antisense oligonucleotide had a HindIII restriction enzyme site incorporated into it. PCR using rat brain cDNA as template was performed using standard techniques (e.g. Whiting et al., *Proc. Natl. Acad. Sci. USA*, 1990, 87, 9966–9970) to yield PCR products of 185 and 950 bases in length (N-terminal cDNA probe and C-terminal cDNA probe, respectively). These were subcloned into pBluescript Sk$^-$ (Stratagene). A human hippocampal cDNA library (Stratagene) was screened under moderate stringency conditions (42° C. in 5×SSPE, 5×Denhardt's solution, 100 mg/ml salmon sperm DNA, 0.1% sodium dodecyl sulphate, 30% formamide) using standard techniques (e.g. Maniatis et al., in *Molecular Cloning: A Laboratory Manual*, Cold Spring Harbor Press, New York, 2nd edition, 1989). A number of cDNA clones were isolated and characterised. These cDNAs encoded the entire human NMDA R2A receptor subunit, with the exception of a sequence spanning bases approx. 300–900 of the coding region. This missing sequence was obtained by PCR: oligonucleotide primers derived from the 5' untranslated region of the human NMDA R2A receptor subunit cDNA sequence SEQ ID NO:20 (5'CCCCACTGCATCCGGTACCTTCTCGGGCTACA3') and the coding region of the human NMDA R2A receptor subunit cDNA sequence, FIGS. 4A to 4J, bases 873–902 SEQ ID NO:21 (5'AGTCCCAGTCATATGAGACAGAAATGA3'), were used to generate a 5' cDNA fragment using human hippocampal cDNA as template. A full-length human NMDA R2A receptor subunit cDNA was generated by assembling overlapping cDNAs using standard molecular biology techniques, and the 5' cDNA fragment generated by PCR and sequenced on both strands using Taq dideoxy terminator cycle sequencing (Applied BioSystems) and an Applied BioSystems 373A DNA Sequencer. The complete nucleotide and deduced amino acid sequence is shown in FIGS. 4A to 4J (SEQ ID NO:9 and 10)

EXAMPLE 3

Preparation of R1a transfected Cells and R1a+R2A Transfected Cells a) Construction of Eukaryotic Expression Vector pMSGneo The approx. 2500 base pair HindIII-EcoRI fragment of the vector pMSG (purchased from Pharmacia Biosystems Limited, Milton Keynes, United Kingdom), containing the gpt structural gene and SV40 polyadenylation signals was replaced by the approx. 2800 base pair HindIII-EcoRI fragment of pSV2neo (Southern, P. J. and Berg, P. J., *Molecular and Applied Genetics*, 1, 327–341, 1982) containing the neomycin resistance gene Neo$^r$ and SV40 polyadenylation signals. The EcoRI and HindIII sites were then removed by restriction digesting, blunt ending with klenow polymerase, and religating. EcoRI and HindIII cloning sites were then inserted at the XhoI and SmaI sites of the polylinker by conventional techniques using EcoRI and HindIII linkers.

b) Cloning of Subunit cDNAs into pMSGneo

Human R1a and R2A cDNA were cloned as described in Examples 1 and 2 above respectively. Human R1a was subcloned from pBluescript Sk$^-$ (Stratagene, San Diego, Calif., USA) by digestion with SalI and EcoRI and ligation into the SalI and EcoRI sites of pMSGneo. Human R2A was subcloned from pBluescript Sk⁻ by restriction digestion with NheI and XhoI and ligation into the NheI and XhoI sites of pMSGneo.

c) Co-transfection of Mouse Ltk⁻ Cells

Ltk⁻ cells were obtained from the Salk Institute for Biological Studies, San Diego, Calif. Cells were grown at 37° C., 5–8% $CO_2$, in Modified Eagles Medium containing penicillin, streptomycin and 10% fetal calf serum. The expression vector harbouring the NMDA receptor subunit DNAs for co-transfection was prepared by a standard protocol (Chen, C. and Okayama, H., *BioTechniques*, 6, 632–638, 1988). For co-transfection, Ltk⁻ cells were plated in dishes (approx. $2 \times 10^5$ cells/dish) and grown overnight. The transfection was performed by calcium phosphate precipitation using a kit (purchased from 5 Prime→3 Prime Products, Westchester, Pa.). Co-transfection was performed according to manufacturers' instructions, using 5 µg of each subunit DNA construct per 10 cm dish of cells. After 2 days in culture the cells were divided 1:8 into culture medium containing 1 mg/ml neomycin [Geneticin (obtainable from Gibco BRL, Paisley, Scotland, United Kingdom)]. After a further week the concentration was increased to 1.5 mg/ml, and then 2 mg/ml 1 week after that. Resistant clones of cells were isolated and subcloned using cloning cylinders. Subclones were analysed using radioligand binding: subclones were grown in 10 cm culture dishes, and when confluent changed into culture medium containing 1 µM dexamethasone (obtainable from Sigma Chemical Company, Poole, Dorset, United Kingdom). In order to prevent cell death induced by the expression of the recombinant R1a+R2A receptor, 10 mM $MgCl_2$ and 100 µM D-AP5 (D-2-amino-5-phosphonovalerate) (Tocris-Neuramin, Essex, United Kingdom) were added into the culture medium in addition to the dexamethasone. $MgCl_2$ and D-AP5 are substances known to act as antagonists at the NMDA receptor (Wong and Kemp, *Ann. Rev. Pharmacol. Toxicol.*, 1991, 31, 401). 3–5 days later the cells were harvested, membranes prepared and used for radioligand binding (see Example 4, step (a) below), using the glycine site antagonist [$^3$H]-L- 689,560 (custom synthesised by Amersham International p1c, Amersham, United Kingdom) for the characterisation of the recombinant R1 receptor, and the channel blocker [$^3$H]-dizocilpine (obtained from New England Nuclear, Du Pont Ltd., Stevenage, United Kingdom) for the characterisation of the recombinant R1a+R2A receptor.

The recombinant R1a receptor clone expressing the highest amount of [$^3$H]-L-689,560 binding was subcloned from a single cell by limiting dilution. The resultant clonal population of these cells is referred to hereinbelow as population A.

The recombinant R1a+R2A receptor clone expressing the highest amount of [$^3$H]-dizocilpine binding was subcloned from a single cell by limiting dilution. The resultant clonal population of these cells is referred to hereinbelow as population B.

EXAMPLE 4

Characterization of R1a Transfected Cells and R1a+R2A Transfected Cells a) Radioligand Binding The nature of the recombinant R1a NMDA receptors prepared as described in Example 3 was addressed by characterization of the glycine site binding pharmacology, using the glycine site antagonist [$^3$H]-L-689,560. For radio-ligand binding assays, cells which had been induced by culture in dexamethasone containing medium for 3–5 days were scraped off into 5 mM Tris-Acetate, pH 7.0 at 4° C. (buffer 1) and pelleted (20,000 rpm, Sorvall RC5C centrifuge). The cell pellet was resuspended in buffer 1, homogenised using an Ultra-Turrax homogeniser and then pelleted as above. This was repeated once more, and the cells then resuspended in 50 mM Tris-Acetate, pH 7.0 at 4° C. (buffer 2) at a protein concentration of 1 mg/ml. Radioligand binding was performed in 0.5 ml final volume buffer 2, containing 1 nM of [$^3$H]-L-689,560 and 100 µg of protein. After 2 hours incubation on ice the membranes were harvested onto filters using a Brandel cell harvester, washed with cold buffer 2, and bound radioactivity determined by scintillation counting. Non-specific binding was determined in a parallel incubation containing 10 mM glycine. The recombinant R1a receptors bound [$^3$H]-L-689,560 at levels of up to 3700 fmols/mg protein. No binding was seen to untransfected Ltk⁻ cells, confirming that the [$^3$H]-L-689,560 was binding to recombinant R1 NMDA receptors.

The nature of the recombinant R1a+R2A NMDA receptors prepared as described in Example 3 was addressed by demonstrating binding of the channel blocker [$^3$H]-dizocilpine. For radioligand binding assays, cells which had been induced by culture in dexamethasone, $MgCl_2$ and D-AP5 containing medium for 3–5 days were scraped off into 5 mM Tris-Acetate, pH 7.0 at 4° C. (buffer 1) and pelleted (20,000 rpm, Sorvall RC5C centrifuge). The cell pellet was resuspended in buffer 1, homogenised using an Ultra-Turrax homogeniser and then pelleted as above. This was repeated once more, and the cells then resuspended in 5 mM Tris-Acetate, pH 7.4 at 25° C. (buffer 3) at a protein concentration of 1 mg/ml. Radioligand binding was performed in 0.5 ml final volume buffer 3, containing 2 nM of [$^3$H]-dizocilpine and 100 µg of protein. After 2 hours at 25° C. in the presence of 30 µM glycine and 30 µM L-glutamate the membranes were washed with buffer 1 and bound radioactivity determined by scintillation counting. The recombinant R1a+R2A receptors bound [$^3$H]-dizocilpine at levels up to 200 fmols/mg protein. No binding was seen to untransfected Ltk⁻ cells, confirming that the [$^3$H]-dizocilpine was binding to recombinant R1a+R2A NMDA receptors. Non-specific binding was determined in a parallel incubation containing 100 µM dizocilpine. The recombinant R1a+R2A receptors bound also [$^3$H]-L-689,560 at levels of up to 500 fmols/mg protein, confirming the presence of a glycine binding site in population B cells.

b) Electrophysiology

The nature of the NMDA receptor expressed by population B cells has been extensively characterised by electrophysiological techniques, using whole cell patch clamp. Only cells induced by culture in the presence of dexamethasone showed responses to NMDA. Concentration response curves to glutamate in a saturating concentration of glycine (10 µM) gave a log $EC_{50}$ of 5.77, and a Hill coefficient of 1.1. The response to glutamate and glycine was antagonised by the competitive glutamate receptor antagonist CGS 19,755 (Research Biochemical International, MA, USA). All these electrophysiological data confirm that the recombinant R1a+R2A NMDA receptor expressed by population B cells has the properties expected of a bona fide NMDA receptor.

What is claimed is:

1. A recombinant DNA molecule having a nucleotide sequence selected from the group consisting of SEQ ID NO:9, SEQ ID NO:11, SEQ ID NO:12 and SEQ ID NO 13.

2. An expression vector comprising a DNA molecule of claim 1.

3. A recombinant cell line comprised of a host cell transformed with an expression vector of claim 2.

4. A recombinantly produced NMDA receptor subunit, wherein said subunit is expressed from an expression vector, wherein said vector comprises a DNA molecule having a nucleotide sequence selected from the group consisting of SEQ ID NO:9, SEQ ID NO:11, SEQ ID NO:12 and SEQ ID NO:13.

* * * * *

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 2621 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
GCCGCGCAGA GCCAGGCCCG CGGCCCGAGC CCATGAGCAC CATGCGCCTG TTGACGCTCG     60
CCCTGCTGTT CTCCTGCTCC CTCGCCCGTG CCGCGTGCGA CCCCAAGATC GTCAACATTG    120
GCGCGGTGCT GAGCACGCGG AAGCACGAGC AGATGTTCCG CGAGGCCGTG AACCAGGCCA    180
ACAAGCGGCA CGGCTCCTGG AAGATTCAGC TCAATGCCAC CTCCGTCACG CACAAGCCCA    240
ACGCCATCCA GATGGCTCTG TCGGTGTGCG AGGACCTCAT CTCCAGCCAG GTCTACGCCA    300
TCCTAGTTAG CCATCCACCT ACCCCCAACG ACCACTTCAC TCCCACCCCT GTCTCCTACA    360
CAGCCGGCTT CTACCGCATA CCCGTGCTGG GGCTGACCAC CCGCATGTCC ATCTACTCGG    420
ACAAGAGCAT CCACCTGAGC TTCCTGCGCA CCGTGCCGCC CTACTCCCAC CAGTCCAGCG    480
TGTGGTTTGA GATGATGCGT GTCTACAGCT GGAACCACAT CATCCTGCTG GTCAGCGACG    540
ACCACGAGGG CCGGGCGGCT CAGAAACGCC TGGAGACGCT GCTGGAGGAG CGTGAGTCCA    600
AGGCAGAGAA GGTGCTGCAG TTTGACCCAG GGACCAAGAA CGTGACGGCC CTGCTGATGG    660
AGGCGAAAGA GCTGGAGGCC CGGGTCATCA TCCTTTCTGC CAGCGAGGAC GATGCTGCCA    720
CTGTATACCG CGCAGCCGCG ATGCTGAACA TGACGGGCTC CGGGTACGTG TGGCTGGTCG    780
GCGAGCGCGA GATCTCGGGG AACGCCCTGG CCTACGCCCC AGACGGCATC CTCGGGCTGC    840
AGCTCATCAA CGGCAAGAAC GAGTCGGCCC ACATCAGCGA CGCCGTGGGC GTGGTGGCCC    900
AGGCCGTGCA CGAGCTCCTC GAGAAGGAGA ACATCACCGA CCCGCCGCGG GGCTGCGTGG    960
GCAACACCAA CATCTGGAAG ACCGGGCCGC TCTTCAAGAG AGTGCTGATG TCTTCCAAGT   1020
ATGCGGATGG GGTGACTGGT CGCGTGGAGT TCAATGAGGA TGGGGACCGG AAGTTCGCCA   1080
ACTACAGCAT CATGAACCTG CAGAACCGCA AGCTGGTGCA AGTGGGCATC TACAATGGCA   1140
CCCACGTCAT CCCTAATGAC AGGAAGATCA TCTGGCCAGG CGGAGAGACA GAGAAGCCTC   1200
GAGGGTACCA GATGTCCACC AGACTGAAGA TTGTGACGAT CCACCAGGAG CCCTTCGTGT   1260
ACGTCAAGCC CACGCTGAGT GATGGGACAT GCAAGGAGGA GTTCACAGTC AACGGCGACC   1320
CAGTCAAGAA GGTGATCTGC ACCGGGCCCA ACGACACGTC GCCGGGCAGC CCCCGCCACA   1380
CGGTGCCTCA GTGTTGCTAC GGCTTTTGCA TCGACCTGCT CATCAAGCTG GCACGGACCA   1440
TGAACTTCAC CTACGAGGTG CACCTGGTGG CAGATGGCAA GTTCGGCACA CAGGAGCGGG   1500
TGAACAACAG CAACAAGAAG GAGTGGAATG GGATGATGGG CGAGCTGCTC AGCGGGCAGG   1560
CAGACATGAT CGTGGCGCCG CTAACCATAA ACAACGAGCG CGCGCAGTAC ATCGAGTTTT   1620
CCAAGCCCTT CAAGTACCAG GGCCTGACTA TTCTGGTCAA GAAGGAGATT CCCCGGAGCA   1680
CGCTGGACTC GTTCATGCAG CCGTTCCAGA GCACACTGTG GCTGCTGGTG GGGCTGTCGG   1740
TGCACGTGGT GGCCGTGATG CTGTACCTGC TGGACCGCTT CAGCCCCTTC GGCCGGTTCA   1800
```

```
AGGTGAACAG CGAGGAGGAG GAGGAGGACG CACTGACCCT GTCCTCGGCC ATGTGGTTCT    1860

CCTGGGGCGT CCTGCTCAAC TCCGGCATCG GGGAAGGCGC CCCCAGAAGC TTCTCAGCGC    1920

GCATCCTGGG CATGGTGTGG GCCGGCTTTG CCATGATCAT CGTGGCCTCC TACACTGCCA    1980

ACTTGGCGGC CTTCCTGGTG CTGGACCGGC CGGAGGAGCG CATCACGGGC ATCAACGACC    2040

CTCGGCTGAG GAACCCCTCG GACAAGTTTA TCTACGCCAC GGTGAAGCAG AGCTCCGTGG    2100

ATATCTACTT CCGGCGCCAG GTGGAGCTGA GCACCATGTA CCGGCATATG GAGAAGCACA    2160

ACTACGAGAG TGCGGCGGAG GCCATCCAGG CCGTGAGAGA CAACAAGCTG CATGCCTTCA    2220

TCTGGGACTC GGCGGTGCTG GAGTTCGAGG CCTCGCAGAA GTGCGACCTG GTGACGACTG    2280

GAGAGCTGTT TTTCCGCTCG GGCTTCGGCA TAGGCATGCG CAAAGACAGC CCCTGGAAGC    2340

AGAACGTCTC CCTGTCCATC CTCAAGTCCC ACGAGAATGG CTTCATGGAA GACCTGGACA    2400

AGACGTGGGT TCGGTATCAG GAATGTGACT CGCGCAGCAA CGCCCCTGCA ACCCTTACTT    2460

TTGAGAACAT GGCCGGGGTC TTCATGCTGG TAGCTGGGGG CATCGTGGCC GGGATCTTCC    2520

TGATTTTCAT CGAGATTGCC TACAAGCGGC ACAAGGATGC TCGCCGGAAG CAGATGCAGC    2580

TGGCCTTTGC CGCCGTTAAC GTGTGGCGGA AGAACCTGCA G                        2621

(2) INFORMATION FOR SEQ ID NO:2:

(i) SEQUENCE CHARACTERISTICS:
        (A) LENGTH: 863 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:2:

Met Ser Thr Met Arg Leu Leu Thr Leu Ala Leu Leu Phe Ser Cys Ser
1               5                   10                  15

Leu Ala Arg Ala Ala Cys Asp Pro Lys Ile Val Asn Ile Gly Ala Val
                20                  25                  30

Leu Ser Thr Arg Lys His Glu Gln Met Phe Arg Glu Ala Val Asn Gln
            35                  40                  45

Ala Asn Lys Arg His Gly Ser Trp Lys Ile Gln Leu Asn Ala Thr Ser
        50                  55                  60

Val Thr His Lys Pro Asn Ala Ile Gln Met Ala Leu Ser Val Cys Glu
65                  70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
                100                 105                 110

Phe Tyr Arg Ile Pro Val Leu Gly Leu Thr Thr Arg Met Ser Ile Tyr
            115                 120                 125

Ser Asp Lys Ser Ile His Leu Ser Phe Leu Arg Thr Val Pro Pro Tyr
        130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ala Glu
            180                 185                 190

Lys Val Leu Gln Phe Asp Pro Gly Thr Lys Asn Val Thr Ala Leu Leu
```

-continued

```
                195                 200                 205
Met Glu Ala Lys Glu Leu Glu Ala Arg Val Ile Ile Leu Ser Ala Ser
            210                 215                 220
Glu Asp Ala Ala Thr Val Tyr Arg Ala Ala Met Leu Asn Met
225                 230                 235                 240
Thr Gly Ser Gly Tyr Val Trp Leu Val Gly Glu Arg Glu Ile Ser Gly
                245                 250                 255
Asn Ala Leu Ala Tyr Ala Pro Asp Gly Ile Leu Gly Leu Gln Leu Ile
                260                 265                 270
Asn Gly Lys Asn Glu Ser Ala His Ile Ser Asp Ala Gly Val Val
            275                 280                 285
Ala Gln Ala Val His Glu Leu Leu Glu Lys Glu Asn Ile Thr Asp Pro
            290                 295                 300
Pro Arg Gly Cys Val Gly Asn Thr Asn Ile Trp Lys Thr Gly Pro Leu
305                 310                 315                 320
Phe Lys Arg Val Leu Met Ser Ser Lys Tyr Ala Asp Gly Val Thr Gly
                325                 330                 335
Arg Val Glu Phe Asn Glu Asp Gly Asp Arg Lys Phe Ala Asn Tyr Ser
                340                 345                 350
Ile Met Asn Leu Gln Asn Arg Lys Leu Val Gln Val Gly Ile Tyr Asn
            355                 360                 365
Gly Thr His Val Ile Pro Asn Asp Arg Lys Ile Ile Trp Pro Gly Gly
            370                 375                 380
Glu Thr Glu Lys Pro Arg Gly Tyr Gln Met Ser Thr Arg Leu Lys Ile
385                 390                 395                 400
Val Thr Ile His Gln Glu Pro Phe Val Tyr Val Lys Pro Thr Leu Ser
                405                 410                 415
Asp Gly Thr Cys Lys Glu Glu Phe Thr Val Asn Gly Asp Pro Val Lys
                420                 425                 430
Lys Val Ile Cys Thr Gly Pro Asn Asp Thr Ser Pro Gly Ser Pro Arg
            435                 440                 445
His Thr Val Pro Gln Cys Cys Tyr Gly Phe Cys Ile Asp Leu Leu Ile
            450                 455                 460
Lys Leu Ala Arg Thr Met Asn Phe Thr Tyr Glu Val His Leu Val Ala
465                 470                 475                 480
Asp Gly Lys Phe Gly Thr Gln Glu Arg Val Asn Asn Ser Asn Lys Lys
                485                 490                 495
Glu Trp Asn Gly Met Met Gly Glu Leu Leu Ser Gly Gln Ala Asp Met
            500                 505                 510
Ile Val Ala Pro Leu Thr Ile Asn Asn Glu Arg Ala Gln Tyr Ile Glu
            515                 520                 525
Phe Ser Lys Pro Phe Lys Tyr Gln Gly Leu Thr Ile Leu Val Lys Lys
530                 535                 540
Glu Ile Pro Arg Ser Thr Leu Asp Ser Phe Met Gln Pro Phe Gln Ser
545                 550                 555                 560
Thr Leu Trp Leu Leu Val Gly Leu Ser Val His Val Val Ala Val Met
                565                 570                 575
Leu Tyr Leu Leu Asp Arg Phe Ser Pro Phe Gly Arg Phe Lys Val Asn
            580                 585                 590
Ser Glu Glu Glu Glu Asp Ala Leu Thr Leu Ser Ser Ala Met Trp
            595                 600                 605
Phe Ser Trp Gly Val Leu Leu Asn Ser Gly Ile Gly Glu Gly Ala Pro
            610                 615                 620
```

```
Arg Ser Phe Ser Ala Arg Ile Leu Gly Met Val Trp Ala Gly Phe Ala
625                 630                 635                 640

Met Ile Ile Val Ala Ser Tyr Thr Ala Asn Leu Ala Ala Phe Leu Val
                645                 650                 655

Leu Asp Arg Pro Glu Glu Arg Ile Thr Gly Ile Asn Asp Pro Arg Leu
                660                 665                 670

Arg Asn Pro Ser Asp Lys Phe Ile Tyr Ala Thr Val Lys Gln Ser Ser
                675                 680                 685

Val Asp Ile Tyr Phe Arg Arg Gln Val Glu Leu Ser Thr Met Tyr Arg
                690                 695                 700

His Met Glu Lys His Asn Tyr Glu Ser Ala Ala Glu Ala Ile Gln Ala
705                 710                 715                 720

Val Arg Asp Asn Lys Leu His Ala Phe Ile Trp Asp Ser Ala Val Leu
                725                 730                 735

Glu Phe Glu Ala Ser Gln Lys Cys Asp Leu Val Thr Thr Gly Glu Leu
                740                 745                 750

Phe Phe Arg Ser Gly Phe Gly Ile Gly Met Arg Lys Asp Ser Pro Trp
                755                 760                 765

Lys Gln Asn Val Ser Leu Ser Ile Leu Lys Ser His Glu Asn Gly Phe
                770                 775                 780

Met Glu Asp Leu Asp Lys Thr Trp Val Arg Tyr Gln Glu Cys Asp Ser
785                 790                 795                 800

Arg Ser Asn Ala Pro Ala Thr Leu Thr Phe Glu Asn Met Ala Gly Val
                805                 810                 815

Phe Met Leu Val Ala Gly Gly Ile Val Ala Gly Ile Phe Leu Ile Phe
                820                 825                 830

Ile Glu Ile Ala Tyr Lys Arg His Lys Asp Ala Arg Arg Lys Gln Met
                835                 840                 845

Gln Leu Ala Phe Ala Ala Val Asn Val Trp Arg Lys Asn Leu Gln
                850                 855                 860

(2) INFORMATION FOR SEQ ID NO:3:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

GATAGAAAGA GTGGTAGAGC AGAGCCTGAC CCTAAAAAGA AAGCCACATT TAGGGCTATC      60

ACCTCCACCC TGGCTTCCAG CTTCAAGAGG CGTAGGTCCT CCAAAGACAC G             111

(2) INFORMATION FOR SEQ ID NO:4:

(i) SEQUENCE CHARACTERISTICS:
        (A) LENGTH: 37 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:4:

Asp Arg Lys Ser Gly Arg Ala Glu Pro Asp Pro Lys Lys Lys Ala Thr
1               5                   10                  15
```

Phe Arg Ala Ile Thr Ser Thr Leu Ala Ser Ser Phe Lys Arg Arg Arg
            20                  25                  30

Ser Ser Lys Asp Thr
        35

(2) INFORMATION FOR SEQ ID NO:5:

(i) SEQUENCE CHARACTERISTICS:
        (A) LENGTH: 184 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

AGCACCGGGG GTGGACGCGG CGCTTTGCAA AACCAAAAAG ACACAGTGCT GCCGCGACGG        60

CCTATTGAGA GGGAGGAGGG CCAGCTGCAG CTGTGTTCCC GTCATAGGGA GAGCTGAGAC       120

TCCCCGCCCG CCCTCCTCTG CCCCCCTCCC CCGCAGACAG ACAGACAGAC GGACGGGACA       180

GCGG                                                                   184

(2) INFORMATION FOR SEQ ID NO:6:

(i) SEQUENCE CHARACTERISTICS:
        (A) LENGTH: 38 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:6:

Ser Thr Gly Gly Gly Arg Gly Ala Leu Gln Asn Gln Lys Asp Thr Val
1               5                   10                  15

Leu Pro Arg Arg Pro Ile Glu Arg Glu Glu Gly Gln Leu Gln Leu Cys
            20                  25                  30

Ser Arg His Arg Glu Ser
        35

(2) INFORMATION FOR SEQ ID NO:7:

(i) SEQUENCE CHARACTERISTICS:
        (A) LENGTH: 103 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

CAGTACCATC CCACTGATAT CACGGGCCCG CTCAACCTCT CAGATCCCTC GGTCAGCACC        60

GTGGTGTGAG GCCCCCGGAG CGCCCACCTG CCCAGTTTAG CCC                        103

(2) INFORMATION FOR SEQ ID NO:8:

(i) SEQUENCE CHARACTERISTICS:
        (A) LENGTH: 22 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:8:

```
Gln Tyr His Pro Thr Asp Ile Thr Gly Pro Leu Asn Leu Ser Asp Pro
1               5                   10                  15

Ser Val Ser Thr Val Val
            20
```

(2) INFORMATION FOR SEQ ID NO:9:

(i) SEQUENCE CHARACTERISTICS:
        (A) LENGTH: 4858 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
CTGCATCCTC GACCTTCTCG GGCTACAGGG ACCGTCAGTG GCGACTATGG GCAGAGTGGG      60

CTATTGGACC CTGCTGGTGC TGCCGGCCCT TCTGGTCTGG CGCGGTCCGG CGCCGAGCGC     120

GGCGGCGGAG AAGGGTCCCC CCGCGCTAAA TATTGCGGTG ATGCTGGGTC ACAGCCACGA     180

CGTGACAGAG CGCGAACTTC GAACACTGTG GGGCCCCGAG CAGGCGGGCG GGCTGCCCCT     240

GGACGTGAAC GTGGTAGCTC TGCTGATGAA CCGCACCGAC CCCAAGAGCC TCATCACGCA     300

CGTGTGCGAC CTCATGTCCG GGCACGCAT CCACGGCCTC GTGTTTGGGG ACGACACGGA      360

CCAGGAGGTC GTAGCCCAGA TGCTGGATTT TATCTCCTCC CACACCTTCG TCCCCATCTT     420

GGGCATTCAT GGGGGCGCAT CTATGATCAT GGCTGACAAG GATCCGACGT CTACCTTCTT     480

CCAGTTTGGA GCGTCCATCC AGCAGCAAGC CACGGTCATG CTGAAGATCA TGCAGGATTA     540

TGACTGGCAT GTCTTCTCCC TGGTGACCAC TATCTTCCCT GGCTACAGGG AATTCATCAG     600

CTTCGTCAAG ACCACAGTGG ACAACAGCTT TGTGGGCTGG ACATGCAGA ATGTGATCAC      660

ACTGGACACT TCCTTTGAGG ATGCAAAGAC ACAAGTCCAG CTGAAGAAGA TCCACTCTTC     720

TGTCATCTTG CTCTACTGTT CCAAAGACGA GGCTGTTCTC ATTCTGAGTG AGGCCCGCTC     780

CCTTGGCGTC ACCGGGTATG ATTTCTTCTG GATTGTCCCC AGCTTGGTCT CTGGGAACAC     840

GGAGCTCATC CCAAAAGAGT TTCCATCGGG ACTCATTTCT GTCTCCTACG ATGACTGGGA     900

CTACAGCCTG GAGGCGAGAG TGAGGGACGG CATTGGCATC CTAACCACCG CTGCATCTTC     960

TATGCTGGAG AAGTTCTCCT ACATCCCCGA GGCCAAGGCC AGCTGCTACG GCAGATGGA     1020

GAGGCCAGAG GTCCCGATGC ACACCTTGCA CCCATTTATG GTCAATGTTA CATGGGATGG    1080

CAAAGACTTA TCCTTCACTG AGGAAGGCTA CCAGGTGCAC CCCAGGCTGG TGGTGATTGT    1140

GCTGAACAAA GACCGGGAAT GGGAAAAGGT GGCCAAGTGG AAGAACAATA CGCTGAGCCT    1200

GAGCCACGCC GTGTGGCCCA GGTACAAGTC CTTCTCCGAC TGTGAGCCGG ATGACAACCA    1260

TCTCAGCATC GTCACCCTGG AGGAGGCCCC ATTCGTCATC GTGGAAGACA TAGACCCCCT    1320

GACCGAGACG TGTGTGAGGA ACACCGTGCC ATGTCGGAAG TTCGTCAAAA TCAACAATTC    1380

AACCAATGAG GGGATGAATG TGAAGAAATG CTGCAAGGGG TTCTGCATTG ATATTCTGAA    1440

GAAGCTTTCC AGAACTGTGA AGTTTACTTA CGACCTCTAT CTGGTGACCA ATGGGAAGCA    1500

TGGCAAGAAA GTTAACAATG TGTGGAATGG AATGATCGGT GAAGTGGTCT ATCAACGGGC    1560

AGTCATGGCA GTTGGCTCGC TCACCATCAA TGAGGAACGT TCTGAAGTGG TGGACTTCTC    1620

TGTGCCCTTT GTGGAAACGG GAATCAGTGT CATGGTTTCA AGAAGTAATG GCACCGTCTC    1680

ACCTTCTGCT TTTCTAGAAC CATTCAGCGC CTCTGTCTGG GTGATGATGT TTGTGATGCT    1740

GCTCATTGTT TCTGCCATAG CTGTTTTTGT CTTTGAATAC TTCAGCCCTG TTGGATACAA    1800
```

```
CAGAAACTTA GCCAAAGGGA AAGCACCCCA TGGGCCTTCT TTTACAATTG GAAAAGCTAT   1860

ATGGCTTCTT TGGGGCCTGG TGTTCAATAA CTCCGTGCCT GTCCAGAATC CTAAAGGGAC   1920

CACCAGCAAG ATCATGGTAT CTGTATGGGC CTTCTTCGCT GTCATATTCC TGGCTAGCTA   1980

CACAGCCAAT CTGGCTGCCT TCATGATCCA AGAGGAATTT GTGGACCAAG TGACCGGCCT   2040

CAGTGACAAA AAGTTTCAGA GACCTCATGA CTATTCCCCA CCTTTTCGAT TTGGGACAGT   2100

GCCTAATGGA AGCACGGAGA GAAACATTCG GAATAACTAT CCCTACATGC ATCAGTACAT   2160

GACCAAATTT AATCAGAAAG GAGTAGAGGA CGCCTTGGTC AGCCTGAAAA CGGGGAAGCT   2220

GGACGCTTTC ATCTACGATG CCGCAGTCTT GAATTACAAG GCTGGGAGGG ATGAAGGCTG   2280

CAAACTGGTG ACCATCGGGA GTGGGTACAT CTTTGCCACC ACCAGTTATG GAATTGCCCT   2340

TCAGAAAGGC TCTCCTTGGA AGAGGCAGAT CGACCTGGCC TTGCTTCAGT TTGTGGGTGA   2400

TGGTGAGATG GAGGAGCTGG AGACCCTGTG GCTCACTGGG ATCGTCCACA ACGAGAAGAA   2460

CGAGGTGATG AGCAACCAGC TGGACATTGA CAACATGGCG GGCGTATTCT ACATGCTGGC   2520

TGCCGCCATG GCCCTTAGCC TCATCACCTT CATCTGGGAG CACCTCTTCT ACTGGAAGCT   2580

GCGCTTCTGT TTCACGGGCG TGTGCTCCGA CCGGCCTGGG TTGCTCTTCT CCATCAGCAG   2640

GGGCATCTAC AGCTGCATTC ATGGAGTGCA CATTGAAGAA AAGAAGAAGT CTCCAGACTT   2700

CAATCTGACG GGATCCCAGA GCAACATGTT AAAACTCCTC CGGTCAGCCA AAAACATTTC   2760

CAGCATGTCC AACATGAACT CCTCAAGAAT GGACTCACCC AAAAGAGCTG CTGACTTCAT   2820

CCAAAGAGGT TCCCTCATCA TGGACATGGT TTCAGATAAG GGGAATTTGA TGTACTCAGA   2880

CAACAGGTCC TTTCAGGGGA AAGAGAGCAT TTTTGGAGAC AACATGAACG AACTCCAAAC   2940

ATTTGTGGCC AACCGGCAGA AGGATAACCT CAATAACTAT GTATTCCAGG ACAACATCC    3000

TCTTACTCTC AATGAGTCCA ACCCTAACAC GGTGGAGGTG GCCGTGAGCA CAGAATCCAA   3060

AGCGAACTCT AGACCCCGGC AGCTGTGGAA GAAATCCGTG GATTCCATAC GCCAGGATTC   3120

ACTATCCCAG AATCCAGTCT CCCAGAGGGA TGAGGCAACA GCAGAGAATA GGACCCACTC   3180

CCTAAAGAGC CCTAGGTATC TTCCAGAAGA GATGGCCCAC TCTGACATTT CAGAAACGTC   3240

AAATCGGGCC ACGTGCCACA GGGAACCTGA CAACAGTAAG AACCACAAAA CCAAGGACAA   3300

CTTTAAAAGG TCAGTGGCCT CCAAATACCC CAAGGACTGT AGTGAGGTCG AGCGCACCTA   3360

CCTGAAAACC AAATCAAGCT CCCCTAGAGA CAAGATCTAC ACTATAGATG GTGAGAAGGA   3420

GCCTGGTTTC CACTTAGATC CACCCCAGTT TGTTGAAAAT GTGACCCTGC CGAGAACGT    3480

GGACTTCCCG GACCCCTACC AGGATCCCAG TGAAAACTTC CGCAAGGGGG ACTCCACGCT   3540

GCCAATGAAC CGGAACCCCT TGCATAATGA AGAGGGGCTT TCCAACAACG ACCAGTATAA   3600

ACTCTACTCC AAGCACTTCA CCTTGAAAGA CAAGGGTTCC CCGCACAGTG AGACCAGCGA   3660

GCGATACCGG CAGAACTCCA CGCACTGCAG AAGCTGCCTT TCCAACATGC CCACCTATTC   3720

AGGCCACTTC ACCATGAGGT CCCCCTTCAA GTGCGATGCC TGCCTGCGGA TGGGGAACCT   3780

CTATGACATC GATGAAGACC AGATGCTTCA GGAGACAGGT AACCCAGCCA CCGGGGAGGA   3840

GGTCTACCAG CAGGACTGGG CACAGAACAA TGCCCTTCAA TTACAAAAGA ACAAGCTAAG   3900

GATTAGCCGT CAGCATTCCT ACGATAACAT TGTCGACAAA CCTAGGGAGC TAGACCTTAG   3960

CAGGCCCTCC CGGAGCATAA GCCTCAAGGA CAGGGAACGG CTTCTGGAGG GAAATTTTTA   4020

CGGCAGCCTG TTTAGTGTCC CCTCAAGCAA ACTCTCGGGG AAAAAAGCT  CCCTTTTCCC   4080

CCAAGGTCTG GAGGACAGCA AGAGGAGCAA GTCTCTCTTG CCAGACCACA CCTCCGATAA   4140

CCCTTTCCTC CACTCCCACA GGGATGACCA ACGCTTGGGT ATTGGGAGAT GCCCCTCGGA   4200
```

```
CCCTTACAAA CACTCGTTGC CATCCCAGGC GGTGAATGAC AGCTATCTTC GGTCGTCCTT      4260

GAGGTCAACG GCATCGTACT GTTCCAGGGA CAGTCGGGGC CACAATGATG TGTATATTTC      4320

GGAGCATGTT ATGCCTTATG CTGCAAATAA GAATAATATG TACTCTACCC CCAGGGTTTT      4380

AAATTCCTGC AGCAATAGAC GCGTGTACAA GAAAATGCCT AGTATCGAAT CTGATGTTTA      4440

AAAATCTTCC ATTAATGTTT TATCTATAGG GAAATATACG TAATGGCCAA TGTTCTGGAG      4500

GGTAAATGTT GAATGTCCAA TAGTGCCCTG CTAAGAGGAA GAAGATGTAG GGAGGTATTT      4560

TGTTGTTGTT GTTGTTGGCT CTTTTGCACA CGGCTTCATG CCATAATCTT CCACTCAAGG      4620

AATCTTGTGA GGTGTGTGCT GAGCATGGCA GACACCAGAT AGGTGAGTCC TTAACCAAAA      4680

ATAACTAACT ACATAAGGGC AAGTCTCCGG GACATGCCTA CTGGGTATGT TGCCAATAAT      4740

GATGCATTGG ATGCCAATGG TGATGTTATG ATTTCCTATA TTCCAAATTC CATTAAGGTC      4800

AGCCCACCAT GTAATTTTCT CATCAGAAAT GCCTAATGGT TTCTCTAATA CAGAATAA       4858
```

(2) INFORMATION FOR SEQ ID NO:10:

(i) SEQUENCE CHARACTERISTICS:
        (A) LENGTH: 1464 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:10:

```
Met Gly Arg Val Gly Tyr Trp Thr Leu Leu Val Leu Pro Ala Leu Leu
1               5                   10                  15

Val Trp Arg Gly Pro Ala Pro Ser Ala Ala Glu Lys Gly Pro Pro
            20                  25                  30

Ala Leu Asn Ile Ala Val Met Leu Gly His Ser His Asp Val Thr Glu
            35                  40                  45

Arg Glu Leu Arg Thr Leu Trp Gly Pro Glu Gln Ala Gly Leu Pro
        50                  55                  60

Leu Asp Val Asn Val Val Ala Leu Leu Met Asn Arg Thr Asp Pro Lys
65                  70                  75                  80

Ser Leu Ile Thr His Val Cys Asp Leu Met Ser Gly Ala Arg Ile His
                85                  90                  95

Gly Leu Val Phe Gly Asp Asp Thr Asp Gln Glu Val Val Ala Gln Met
                100                 105                 110

Leu Asp Phe Ile Ser Ser His Thr Phe Val Pro Ile Leu Gly Ile His
            115                 120                 125

Gly Gly Ala Ser Met Ile Met Ala Asp Lys Asp Pro Thr Ser Thr Phe
        130                 135                 140

Phe Gln Phe Gly Ala Ser Ile Gln Gln Gln Ala Thr Val Met Leu Lys
145                 150                 155                 160

Ile Met Gln Asp Tyr Asp Trp His Val Phe Ser Leu Val Thr Thr Ile
                165                 170                 175

Phe Pro Gly Tyr Arg Glu Phe Ile Ser Phe Val Lys Thr Thr Val Asp
                180                 185                 190

Asn Ser Phe Val Gly Trp Asp Met Gln Asn Val Ile Thr Leu Asp Thr
            195                 200                 205

Ser Phe Glu Asp Ala Lys Thr Gln Val Gln Leu Lys Lys Ile His Ser
        210                 215                 220

Ser Val Ile Leu Leu Tyr Cys Ser Lys Asp Glu Ala Val Leu Ile Leu
```

```
                225                 230                 235                 240
Ser Glu Ala Arg Ser Leu Gly Val Thr Gly Tyr Asp Phe Phe Trp Ile
                245                 250                 255
Val Pro Ser Leu Val Ser Gly Asn Thr Glu Leu Ile Pro Lys Glu Phe
                260                 265                 270
Pro Ser Gly Leu Ile Ser Val Ser Tyr Asp Asp Trp Asp Tyr Ser Leu
                275                 280                 285
Glu Ala Arg Val Arg Asp Gly Ile Gly Ile Leu Thr Thr Ala Ala Ser
                290                 295                 300
Ser Met Leu Glu Lys Phe Ser Tyr Ile Pro Glu Ala Lys Ala Ser Cys
305                 310                 315                 320
Tyr Gly Gln Met Glu Arg Pro Glu Val Pro Met His Thr Leu His Pro
                325                 330                 335
Phe Met Val Asn Val Thr Trp Asp Gly Lys Asp Leu Ser Phe Thr Glu
                340                 345                 350
Glu Gly Tyr Gln Val His Pro Arg Leu Val Val Ile Val Leu Asn Lys
                355                 360                 365
Asp Arg Glu Trp Glu Lys Val Ala Lys Trp Lys Asn Asn Thr Leu Ser
                370                 375                 380
Leu Ser His Ala Val Trp Pro Arg Tyr Lys Ser Phe Ser Asp Cys Glu
385                 390                 395                 400
Pro Asp Asp Asn His Leu Ser Ile Val Thr Leu Glu Glu Ala Pro Phe
                405                 410                 415
Val Ile Val Glu Asp Ile Asp Pro Leu Thr Glu Thr Cys Val Arg Asn
                420                 425                 430
Thr Val Pro Cys Arg Lys Phe Val Lys Ile Asn Asn Ser Thr Asn Glu
                435                 440                 445
Gly Met Asn Val Lys Lys Cys Cys Lys Gly Phe Cys Ile Asp Ile Leu
                450                 455                 460
Lys Lys Leu Ser Arg Thr Val Lys Phe Thr Tyr Asp Leu Tyr Leu Val
465                 470                 475                 480
Thr Asn Gly Lys His Gly Lys Lys Val Asn Asn Val Trp Asn Gly Met
                485                 490                 495
Ile Gly Glu Val Val Tyr Gln Arg Ala Val Met Ala Val Gly Ser Leu
                500                 505                 510
Thr Ile Asn Glu Glu Arg Ser Glu Val Val Asp Phe Ser Val Pro Phe
                515                 520                 525
Val Glu Thr Gly Ile Ser Val Met Val Ser Arg Ser Asn Gly Thr Val
                530                 535                 540
Ser Pro Ser Ala Phe Leu Glu Pro Phe Ser Ala Ser Val Trp Val Met
545                 550                 555                 560
Met Phe Val Met Leu Leu Ile Val Ser Ala Ile Ala Val Phe Val Phe
                565                 570                 575
Glu Tyr Phe Ser Pro Val Gly Tyr Asn Arg Asn Leu Ala Lys Gly Lys
                580                 585                 590
Ala Pro His Gly Pro Ser Phe Thr Ile Gly Lys Ala Ile Trp Leu Leu
                595                 600                 605
Trp Gly Leu Val Phe Asn Asn Ser Val Pro Val Gln Asn Pro Lys Gly
                610                 615                 620
Thr Thr Ser Lys Ile Met Val Ser Val Trp Ala Phe Phe Ala Val Ile
625                 630                 635                 640
Phe Leu Ala Ser Tyr Thr Ala Asn Leu Ala Ala Phe Met Ile Gln Glu
                645                 650                 655
```

-continued

```
Glu Phe Val Asp Gln Val Thr Gly Leu Ser Asp Lys Lys Phe Gln Arg
            660                 665                 670

Pro His Asp Tyr Ser Pro Pro Phe Arg Phe Gly Thr Val Pro Asn Gly
            675                 680                 685

Ser Thr Glu Arg Asn Ile Arg Asn Asn Tyr Pro Tyr Met His Gln Tyr
            690                 695                 700

Met Thr Lys Phe Asn Gln Lys Gly Val Glu Asp Ala Leu Val Ser Leu
705                 710                 715                 720

Lys Thr Gly Lys Leu Asp Ala Phe Ile Tyr Asp Ala Ala Val Leu Asn
                    725                 730                 735

Tyr Lys Ala Gly Arg Asp Glu Gly Cys Lys Leu Val Thr Ile Gly Ser
                    740                 745                 750

Gly Tyr Ile Phe Ala Thr Thr Ser Tyr Gly Ile Ala Leu Gln Lys Gly
                    755                 760                 765

Ser Pro Trp Lys Arg Gln Ile Asp Leu Ala Leu Leu Gln Phe Val Gly
                    770                 775                 780

Asp Gly Glu Met Glu Glu Leu Glu Thr Leu Trp Leu Thr Gly Ile Val
785                 790                 795                 800

His Asn Glu Lys Asn Glu Val Met Ser Asn Gln Leu Asp Ile Asp Asn
                    805                 810                 815

Met Ala Gly Val Phe Tyr Met Leu Ala Ala Ala Met Ala Leu Ser Leu
                    820                 825                 830

Ile Thr Phe Ile Trp Glu His Leu Phe Tyr Trp Lys Leu Arg Phe Cys
                    835                 840                 845

Phe Thr Gly Val Cys Ser Asp Arg Pro Gly Leu Leu Phe Ser Ile Ser
850                 855                 860

Arg Gly Ile Tyr Ser Cys Ile His Gly Val His Ile Glu Glu Lys Lys
865                 870                 875                 880

Lys Ser Pro Asp Phe Asn Leu Thr Gly Ser Gln Ser Asn Met Leu Lys
                    885                 890                 895

Leu Leu Arg Ser Ala Lys Asn Ile Ser Ser Met Ser Asn Met Asn Ser
                    900                 905                 910

Ser Arg Met Asp Ser Pro Lys Arg Ala Ala Asp Phe Ile Gln Arg Gly
                    915                 920                 925

Ser Leu Ile Met Asp Met Val Ser Asp Lys Gly Asn Leu Met Tyr Ser
                    930                 935                 940

Asp Asn Arg Ser Phe Gln Gly Lys Glu Ser Ile Phe Gly Asp Asn Met
945                 950                 955                 960

Asn Glu Leu Gln Thr Phe Val Ala Asn Arg Gln Lys Asp Asn Leu Asn
                    965                 970                 975

Asn Tyr Val Phe Gln Gly Gln His Pro Leu Thr Leu Asn Glu Ser Asn
                    980                 985                 990

Pro Asn Thr Val Glu Val Ala Val Ser Thr Glu Ser Lys Ala Asn Ser
                    995                 1000                1005

Arg Pro Arg Gln Leu Trp Lys Lys Ser Val Asp Ser Ile Arg Gln Asp
            1010                1015                1020

Ser Leu Ser Gln Asn Pro Val Ser Gln Arg Asp Glu Ala Thr Ala Glu
1025                1030                1035                1040

Asn Arg Thr His Ser Leu Lys Ser Pro Arg Tyr Leu Pro Glu Glu Met
                    1045                1050                1055

Ala His Ser Asp Ile Ser Glu Thr Ser Asn Arg Ala Thr Cys His Arg
                    1060                1065                1070
```

Glu Pro Asp Asn Ser Lys Asn His Lys Thr Lys Asp Asn Phe Lys Arg
            1075                1080                1085

Ser Val Ala Ser Lys Tyr Pro Lys Asp Cys Ser Glu Val Glu Arg Thr
            1090                1095                1100

Tyr Leu Lys Thr Lys Ser Ser Ser Pro Arg Asp Lys Ile Tyr Thr Ile
1105                1110                1115                1120

Asp Gly Glu Lys Glu Pro Gly Phe His Leu Asp Pro Pro Gln Phe Val
                1125                1130                1135

Glu Asn Val Thr Leu Pro Glu Asn Val Asp Phe Pro Asp Pro Tyr Gln
            1140                1145                1150

Asp Pro Ser Glu Asn Phe Arg Lys Gly Asp Ser Thr Leu Pro Met Asn
            1155                1160                1165

Arg Asn Pro Leu His Asn Glu Glu Gly Leu Ser Asn Asn Asp Gln Tyr
            1170                1175                1180

Lys Leu Tyr Ser Lys His Phe Thr Leu Lys Asp Lys Gly Ser Pro His
1185                1190                1195                1200

Ser Glu Thr Ser Glu Arg Tyr Arg Gln Asn Ser Thr His Cys Arg Ser
            1205                1210                1215

Cys Leu Ser Asn Met Pro Thr Tyr Ser Gly His Phe Thr Met Arg Ser
            1220                1225                1230

Pro Phe Lys Cys Asp Ala Cys Leu Arg Met Gly Asn Leu Tyr Asp Ile
            1235                1240                1245

Asp Glu Asp Gln Met Leu Gln Glu Thr Gly Asn Pro Ala Thr Gly Glu
            1250                1255                1260

Glu Val Tyr Gln Gln Asp Trp Ala Gln Asn Asn Ala Leu Gln Leu Gln
1265                1270                1275                1280

Lys Asn Lys Leu Arg Ile Ser Arg Gln His Ser Tyr Asp Asn Ile Val
            1285                1290                1295

Asp Lys Pro Arg Glu Leu Asp Leu Ser Arg Pro Ser Arg Ser Ile Ser
            1300                1305                1310

Leu Lys Asp Arg Glu Arg Leu Leu Glu Gly Asn Phe Tyr Gly Ser Leu
            1315                1320                1325

Phe Ser Val Pro Ser Ser Lys Leu Ser Gly Lys Lys Ser Ser Leu Phe
1330                1335                1340

Pro Gln Gly Leu Glu Asp Ser Lys Arg Ser Lys Ser Leu Leu Pro Asp
1345                1350                1355                1360

His Thr Ser Asp Asn Pro Phe Leu His Ser His Arg Asp Asp Gln Arg
            1365                1370                1375

Leu Gly Ile Gly Arg Cys Pro Ser Asp Pro Tyr Lys His Ser Leu Pro
            1380                1385                1390

Ser Gln Ala Val Asn Asp Ser Tyr Leu Arg Ser Ser Leu Arg Ser Thr
            1395                1400                1405

Ala Ser Tyr Cys Ser Arg Asp Ser Arg Gly His Asn Asp Val Tyr Ile
            1410                1415                1420

Ser Glu His Val Met Pro Tyr Ala Ala Asn Lys Asn Asn Met Tyr Ser
1425                1430                1435                1440

Thr Pro Arg Val Leu Asn Ser Cys Ser Asn Arg Arg Val Tyr Lys Lys
            1445                1450                1455

Met Pro Ser Ile Glu Ser Asp Val
            1460

(2) INFORMATION FOR SEQ ID NO:11:

(i) SEQUENCE CHARACTERISTICS:

(A) LENGTH: 2916 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

| | | | | | |
|---|---|---|---|---|---|
| GCCGCGCAGA | GCCAGGCCCG | CGGCCCGAGC | CCATGAGCAC | CATGCGCCTG | TTGACGCTCG | 60 |
| CCCTGCTGTT | CTCCTGCTCC | CTCGCCCGTG | CCGCGTGCGA | CCCCAAGATC | GTCAACATTG | 120 |
| GCGCGGTGCT | GAGCACGCGG | AAGCACGAGC | AGATGTTCCG | CGAGGCCGTG | AACCAGGCCA | 180 |
| ACAAGCGGCA | CGGCTCCTGG | AAGATTCAGC | TCAATGCCAC | CTCCGTCACG | CACAAGCCCA | 240 |
| ACGCCATCCA | GATGGCTCTG | TCGGTGTGCG | AGGACCTCAT | CTCCAGCCAG | GTCTACGCCA | 300 |
| TCCTAGTTAG | CCATCCACCT | ACCCCCAACG | ACCACTTCAC | TCCCACCCCT | GTCTCCTACA | 360 |
| CAGCCGGCTT | CTACCGCATA | CCCGTGCTGG | GGCTGACCAC | CCGCATGTCC | ATCTACTCGG | 420 |
| ACAAGAGCAT | CCACCTGAGC | TTCCTGCGCA | CCGTGCCGCC | CTACTCCCAC | CAGTCCAGCG | 480 |
| TGTGGTTTGA | GATGATGCGT | GTCTACAGCT | GGAACCACAT | CATCCTGCTG | GTCAGCGACG | 540 |
| ACCACGAGGG | CCGGGCGGCT | CAGAAACGCC | TGGAGACGCT | GCTGGAGGAG | CGTGAGTCCA | 600 |
| AGGCAGAGAA | GGTGCTGCAG | TTTGACCCAG | GGACCAAGAA | CGTGACGGCC | CTGCTGATGG | 660 |
| AGGCGAAAGA | GCTGGAGGCC | CGGGTCATCA | TCCTTTCTGC | CAGCGAGGAC | GATGCTGCCA | 720 |
| CTGTATACCG | CGCAGCCGCG | ATGCTGAACA | TGACGGGCTC | CGGGTACGTG | TGGCTGGTCG | 780 |
| GCGAGCGCGA | GATCTCGGGG | AACGCCCTGG | CCTACGCCCC | AGACGGCATC | CTCGGGCTGC | 840 |
| AGCTCATCAA | CGGCAAGAAC | GAGTCGGCCC | ACATCAGCGA | CGCCGTGGGC | GTGGTGGCCC | 900 |
| AGGCCGTGCA | CGAGCTCCTC | GAGAAGGAGA | ACATCACCGA | CCCGCCGCGG | GGCTGCGTGG | 960 |
| GCAACACCAA | CATCTGGAAG | ACCGGGCCGC | TCTTCAAGAG | AGTGCTGATG | TCTTCCAAGT | 1020 |
| ATGCGGATGG | GGTGACTGGT | CGCGTGGAGT | TCAATGAGGA | TGGGGACCGG | AAGTTCGCCA | 1080 |
| ACTACAGCAT | CATGAACCTG | CAGAACCGCA | AGCTGGTGCA | AGTGGGCATC | TACAATGGCA | 1140 |
| CCCACGTCAT | CCCTAATGAC | AGGAAGATCA | TCTGGCCAGG | CGGAGAGACA | GAGAAGCCTC | 1200 |
| GAGGGTACCA | GATGTCCACC | AGACTGAAGA | TTGTGACGAT | CCACCAGGAG | CCCTTCGTGT | 1260 |
| ACGTCAAGCC | CACGCTGAGT | GATGGGACAT | GCAAGGAGGA | GTTCACAGTC | AACGGCGACC | 1320 |
| CAGTCAAGAA | GGTGATCTGC | ACCGGGCCCA | ACGACACGTC | GCCGGGCAGC | CCCCGCCACA | 1380 |
| CGGTGCCTCA | GTGTTGCTAC | GGCTTTTGCA | TCGACCTGCT | CATCAAGCTG | GCACGGACCA | 1440 |
| TGAACTTCAC | CTACGAGGTG | CACCTGGTGG | CAGATGGCAA | GTTCGGCACA | CAGGAGCGGG | 1500 |
| TGAACAACAG | CAACAAGAAG | GAGTGGAATG | GGATGATGGG | CGAGCTGCTC | AGCGGGCAGG | 1560 |
| CAGACATGAT | CGTGGCGCCG | CTAACCATAA | ACAACGAGCG | CGCGCAGTAC | ATCGAGTTTT | 1620 |
| CCAAGCCCTT | CAAGTACCAG | GGCCTGACTA | TTCTGGTCAA | GAAGGAGATT | CCCCGGAGCA | 1680 |
| CGCTGGACTC | GTTCATGCAG | CCGTTCCAGA | GCACACTGTG | GCTGCTGGTG | GGGCTGTCGG | 1740 |
| TGCACGTGGT | GGCCGTGATG | CTGTACCTGC | TGGACCGCTT | CAGCCCCTTC | GGCCGGTTCA | 1800 |
| AGGTGAACAG | CGAGGAGGAG | GAGGAGGACG | CACTGACCCT | GTCCTCGGCC | ATGTGGTTCT | 1860 |
| CCTGGGGCGT | CCTGCTCAAC | TCCGGCATCG | GGGAAGGCGC | CCCCAGAAGC | TTCTCAGCGC | 1920 |
| GCATCCTGGG | CATGGTGTGG | GCCGGCTTTG | CCATGATCAT | CGTGGCCTCC | TACACTGCCA | 1980 |
| ACTTGGCGGC | CTTCCTGGTG | CTGGACCGGC | CGGAGGAGCG | CATCACGGGC | ATCAACGACC | 2040 |
| CTCGGCTGAG | GAACCCCTCG | GACAAGTTTA | TCTACGCCAC | GGTGAAGCAG | AGCTCCGTGG | 2100 |

```
ATATCTACTT CCGGCGCCAG GTGGAGCTGA GCACCATGTA CCGGCATATG GAGAAGCACA    2160

ACTACGAGAG TGCGGCGGAG GCCATCCAGG CCGTGAGAGA CAACAAGCTG CATGCCTTCA    2220

TCTGGGACTC GGCGGTGCTG GAGTTCGAGG CCTCGCAGAA GTGCGACCTG GTGACGACTG    2280

GAGAGCTGTT TTTCCGCTCG GGCTTCGGCA TAGGCATGCG CAAAGACAGC CCCTGGAAGC    2340

AGAACGTCTC CCTGTCCATC CTCAAGTCCC ACGAGAATGG CTTCATGGAA GACCTGGACA    2400

AGACGTGGGT TCGGTATCAG GAATGTGACT CGCGCAGCAA CGCCCCTGCA ACCCTTACTT    2460

TTGAGAACAT GGCCGGGGTC TTCATGCTGG TAGCTGGGGG CATCGTGGCC GGGATCTTCC    2520

TGATTTTCAT CGAGATTGCC TACAAGCGGC ACAAGGATGC TCGCCGGAAG CAGATGCAGC    2580

TGGCCTTTGC CGCCGTTAAC GTGTGGCGGA AGAACCTGCA GGATAGAAAG AGTGGTAGAG    2640

CAGAGCCTGA CCCTAAAAAG AAAGCCACAT TTAGGGCTAT CACCTCCACC CTGGCTTCCA    2700

GCTTCAAGAG GCGTAGGTCC TCCAAAGACA CGAGCACCGG GGGTGGACGC GGCGCTTTGC    2760

AAAACCAAAA AGACACAGTG CTGCCGCGAC GGCCTATTGA GAGGGAGGAG GGCCAGCTGC    2820

AGCTGTGTTC CCGTCATAGG GAGAGCTGAG ACTCCCCGCC CGCCCTCCTC TGCCCCCCTC    2880

CCCCGCAGAC AGACAGACAG ACGGACGGGA CAGCGG                              2916

(2) INFORMATION FOR SEQ ID NO:12:

(i) SEQUENCE CHARACTERISTICS:
        (A) LENGTH: 2835 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

GCCGCGCAGA GCCAGGCCCG CGGCCCGAGC CCATGAGCAC CATGCGCCTG TTGACGCTCG      60

CCCTGCTGTT CTCCTGCTCC CTCGCCCGTG CCGCGTGCGA CCCCAAGATC GTCAACATTG     120

GCGCGGTGCT GAGCACGCGG AAGCACGAGC AGATGTTCCG CGAGGCCGTG AACCAGGCCA     180

ACAAGCGGCA CGGCTCCTGG AAGATTCAGC TCAATGCCAC CTCCGTCACG CACAAGCCCA     240

ACGCCATCCA GATGGCTCTG TCGGTGTGCG AGGACCTCAT CTCCAGCCAG GTCTACGCCA     300

TCCTAGTTAG CCATCCACCT ACCCCCAACG ACCACTTCAC TCCCACCCCT GTCTCCTACA     360

CAGCCGGCTT CTACCGCATA CCCGTGCTGG GGCTGACCAC CCGCATGTCC ATCTACTCGG     420

ACAAGAGCAT CCACCTGAGC TTCCTGCGCA CCGTGCCGCC CTACTCCCAC CAGTCCAGCG     480

TGTGGTTTGA GATGATGCGT GTCTACAGCT GGAACCACAT CATCCTGCTG GTCAGCGACG     540

ACCACGAGGG CCGGGCGGCT CAGAAACGCC TGGAGACGCT GCTGGAGGAG CGTGAGTCCA     600

AGGCAGAGAA GGTGCTGCAG TTTGACCCAG GGACCAAGAA CGTGACGGCC CTGCTGATGG     660

AGGCGAAAGA GCTGGAGGCC CGGGTCATCA TCCTTTCTGC CAGCGAGGAC GATGCTGCCA     720

CTGTATACCG CGCAGCCGCG ATGCTGAACA TGACGGGCTC CGGGTACGTG TGGCTGGTCG     780

GCGAGCGCGA GATCTCGGGG AACGCCCTGG CCTACGCCCC AGACGGCATC CTCGGGCTGC     840

AGCTCATCAA CGGCAAGAAC GAGTCGGCCC ACATCAGCGA CGCCGTGGGC GTGGTGGCCC     900

AGGCCGTGCA CGAGCTCCTC GAGAAGGAGA ACATCACCGA CCCGCCGCGG GGCTGCGTGG     960

GCAACACCAA CATCTGGAAG ACCGGGCCGC TCTTCAAGAG AGTGCTGATG TCTTCCAAGT    1020

ATGCGGATGG GGTGACTGGT CGCGTGGAGT TCAATGAGGA TGGGGACCGG AAGTTCGCCA    1080

ACTACAGCAT CATGAACCTG CAGAACCGCA AGCTGGTGCA AGTGGGCATC TACAATGGCA    1140
```

-continued

```
CCCACGTCAT CCCTAATGAC AGGAAGATCA TCTGGCCAGG CGGAGAGACA GAGAAGCCTC    1200

GAGGGTACCA GATGTCCACC AGACTGAAGA TTGTGACGAT CCACCAGGAG CCCTTCGTGT    1260

ACGTCAAGCC CACGCTGAGT GATGGGACAT GCAAGGAGGA GTTCACAGTC AACGGCGACC    1320

CAGTCAAGAA GGTGATCTGC ACCGGGCCCA ACGACACGTC GCCGGGCAGC CCCCGCCACA    1380

CGGTGCCTCA GTGTTGCTAC GGCTTTTGCA TCGACCTGCT CATCAAGCTG GCACGGACCA    1440

TGAACTTCAC CTACGAGGTG CACCTGGTGG CAGATGGCAA GTTCGGCACA CAGGAGCGGG    1500

TGAACAACAG CAACAAGAAG GAGTGGAATG GGATGATGGG CGAGCTGCTC AGCGGGCAGG    1560

CAGACATGAT CGTGGCGCCG CTAACCATAA ACAACGAGCG CGCGCAGTAC ATCGAGTTTT    1620

CCAAGCCCTT CAAGTACCAG GGCCTGACTA TTCTGGTCAA GAAGGAGATT CCCCGGAGCA    1680

CGCTGGACTC GTTCATGCAG CCGTTCCAGA GCACACTGTG GCTGCTGGTG GGGCTGTCGG    1740

TGCACGTGGT GGCCGTGATG CTGTACCTGC TGGACCGCTT CAGCCCCTTC GGCCGGTTCA    1800

AGGTGAACAG CGAGGAGGAG GAGGAGGACG CACTGACCCT GTCCTCGGCC ATGTGGTTCT    1860

CCTGGGGCGT CCTGCTCAAC TCCGGCATCG GGGAAGGCGC CCCCAGAAGC TTCTCAGCGC    1920

GCATCCTGGG CATGGTGTGG GCCGGCTTTG CCATGATCAT CGTGGCCTCC TACACTGCCA    1980

ACTTGGCGGC CTTCCTGGTG CTGGACCGGC CGGAGGAGCG CATCACGGGC ATCAACGACC    2040

CTCGGCTGAG GAACCCCTCG GACAAGTTTA TCTACGCCAC GGTGAAGCAG AGCTCCGTGG    2100

ATATCTACTT CCGGCGCCAG GTGGAGCTGA GCACCATGTA CCGGCATATG GAGAAGCACA    2160

ACTACGAGAG TGCGGCGGAG GCCATCCAGG CCGTGAGAGA CAACAAGCTG CATGCCTTCA    2220

TCTGGGACTC GGCGGTGCTG GAGTTCGAGG CCTCGCAGAA GTGCGACCTG GTGACGACTG    2280

GAGAGCTGTT TTTCCGCTCG GGCTTCGGCA TAGGCATGCG CAAAGACAGC CCCTGGAAGC    2340

AGAACGTCTC CCTGTCCATC CTCAAGTCCC ACGAGAATGG CTTCATGGAA GACCTGGACA    2400

AGACGTGGGT TCGGTATCAG GAATGTGACT CGCGCAGCAA CGCCCCTGCA ACCCTTACTT    2460

TTGAGAACAT GGCCGGGGTC TTCATGCTGG TAGCTGGGGG CATCGTGGCC GGGATCTTCC    2520

TGATTTTCAT CGAGATTGCC TACAAGCGGC ACAAGGATGC TCGCCGGAAG CAGATGCAGC    2580

TGGCCTTTGC CGCCGTTAAC GTGTGGCGGA AGAACCTGCA GGATAGAAAG AGTGGTAGAG    2640

CAGAGCCTGA CCCTAAAAAG AAAGCCACAT TTAGGGCTAT CACCTCCACC CTGGCTTCCA    2700

GCTTCAAGAG GCGTAGGTCC TCCAAAGACA CGCAGTACCA TCCCACTGAT ATCACGGGCC    2760

CGCTCAACCT CTCAGATCCC TCGGTCAGCA CCGTGGTGTG AGGCCCCCGG AGCGCCCACC    2820

TGCCCAGTTT AGCCC                                                    2835
```

(2) INFORMATION FOR SEQ ID NO:13:

(i) SEQUENCE CHARACTERISTICS:
        (A) LENGTH: 2727 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

```
GCCGCGCAGA GCCAGGCCCG CGGCCCGAGC CCATGAGCAC CATGCGCCTG TTGACGCTCG      60

CCCTGCTGTT CTCCTGCTCC CTCGCCCGTG CCGCGTGCGA CCCCAAGATC GTCAACATTG     120

GCGCGGTTGCT GAGCACGCGG AAGCACGAGC AGATGTTCCG CGAGGCCGTG AACCAGGCCA    180

ACAAGCGGCA CGGCTCCTGG AAGATTCAGC TCAATGCCAC CTCCGTCACG CACAAGCCCA    240
```

```
                                              -continued
ACGCCATCCA GATGGCTCTG TCGGTGTGCG AGGACCTCAT CTCCAGCCAG GTCTACGCCA    300

TCCTAGTTAG CCATCCACCT ACCCCCAACG ACCACTTCAC TCCCACCCCT GTCTCCTACA    360

CAGCCGGCTT CTACCGCATA CCCGTGCTGG GGCTGACCAC CCGCATGTCC ATCTACTCGG    420

ACAAGAGCAT CCACCTGAGC TTCCTGCGCA CCGTGCCGCC CTACTCCCAC CAGTCCAGCG    480

TGTGGTTTGA GATGATGCGT GTCTACAGCT GGAACCACAT CATCCTGCTG GTCAGCGACG    540

ACCACGAGGG CCGGGCGGCT CAGAAACGCC TGGAGACGCT GCTGGAGGAG CGTGAGTCCA    600

AGGCAGAGAA GGTGCTGCAG TTTGACCCAG GGACCAAGAA CGTGACGGCC CTGCTGATGG    660

AGGCGAAAGA GCTGGAGGCC CGGGTCATCA TCCTTTCTGC CAGCGAGGAC GATGCTGCCA    720

CTGTATACCG CGCAGCCGCG ATGCTGAACA TGACGGGCTC CGGGTACGTG TGGCTGGTCG    780

GCGAGCGCGA GATCTCGGGG AACGCCCTGG CCTACGCCCC AGACGGCATC CTCGGGCTGC    840

AGCTCATCAA CGGCAAGAAC GAGTCGGCCC ACATCAGCGA CGCCGTGGGC GTGGTGGCCC    900

AGGCCGTGCA CGAGCTCCTC GAGAAGGAGA ACATCACCGA CCCGCCGCGG GGCTGCGTGG    960

GCAACACCAA CATCTGGAAG ACCGGCCGCC TCTTCAAGAG AGTGCTGATG TCTTCCAAGT    1020

ATGCGGATGG GGTGACTGGT CGCGTGGAGT TCAATGAGGA TGGGGACCGG AAGTTCGCCA    1080

ACTACAGCAT CATGAACCTG CAGAACCGCA AGCTGGTGCA AGTGGGCATC TACAATGGCA    1140

CCCACGTCAT CCCTAATGAC AGGAAGATCA TCTGGCCAGG CGGAGAGACA GAGAAGCCTC    1200

GAGGGTACCA GATGTCCACC AGACTGAAGA TTGTGACGAT CCACCAGGAG CCCTTCGTGT    1260

ACGTCAAGCC CACGCTGAGT GATGGGACAT GCAAGGAGGA GTTCACAGTC AACGGCGACC    1320

CAGTCAAGAA GGTGATCTGC ACCGGGCCCA ACGACACGTC GCCGGGCAGC CCCCGCCACA    1380

CGGTGCCTCA GTGTTGCTAC GGCTTTTGCA TCGACCTGCT CATCAAGCTG GCACGGACCA    1440

TGAACTTCAC CTACGAGGTG CACCTGGTGG CAGATGGCAA GTTCGGCACA CAGGAGCGGG    1500

TGAACAACAG CAACAAGAAG GAGTGGAATG GGATGATGGG CGAGCTGCTC AGCGGGCAGG    1560

CAGACATGAT CGTGGCGCCG CTAACCATAA ACAACGAGCG CGCGCAGTAC ATCGAGTTTT    1620

CCAAGCCCTT CAAGTACCAG GGCCTGACTA TTTCGGTCAA GAAGGAGATT CCCCGGAGCA    1680

CGCTGGACTC GTTCATGCAG CCGTTCCAGA GCACACTGTG GCTGCTGGTG GGGCTGTCGG    1740

TGCACGTGGT GGCCGTGATG CTGTACCTGC TGGACCGCTT CAGCCCCTTC GGCCGGTTCA    1800

AGGTGAACAG CGAGGAGGAG GAGGAGGACG CACTGACCCT GTCCTCGGCC ATGTGGTTCT    1860

CCTGGGGCGT CCTGCTCAAC TCCGGCATCG GGGAAGGCGC CCCCAGAAGC TTCTCAGCGC    1920

GCATCCTGGG CATGGTGTGG GCCGGCTTTG CCATGATCAT CGTGGCCTCC TACACTGCCA    1980

ACTTGGCGGC CTTCCTGGTG CTGGACCGGC CGGAGGAGCG CATCACGGGC ATCAACGACC    2040

CTCGGCTGAG GAACCCCTCG GACAAGTTTA TCTACGCCAC GGTGAAGCAG AGCTCCGTGG    2100

ATATCTACTT CCGGCGCCAG GTGGAGCTGA GCACCATGTA CCGGCATATG GAGAAGCACA    2160

ACTACGAGAG TGCGGCGGAG GCCATCCAGG CCGTGAGAGA CAACAAGCTG CATGCCTTCA    2220

TCTGGGACTC GGCCGTGCTG GAGTTCGAGG CCTCGCAGAA GTGCGACCTG GTGACGACTG    2280

GAGAGCTGTT TTTCCGCTCG GGCTTCGGCA TAGGCATGCG CAAAGACAGC CCCTGGAAGC    2340

AGAACGTCTC CCTGTCCATC CTCAAGTCCC ACGAGAATGG CTTCATGGAA GACCTGGACA    2400

AGACGTGGGT TCGGTATCAG GAATGTGACT CGCGCAGCAA CGCCCCTGCA ACCCTTACTT    2460

TTGAGAACAT GGCCGGGGTC TTCATGCTGG TAGCTGGGGG CATCGTGGCC GGGATCTTCC    2520

TGATTTTCAT CGAGATTGCC TACAAGCGGC ACAAGGATGC TCGCCGGAAG CAGATGCAGC    2580

TGGCCTTTGC CGCCGTTAAC GTGTGGCGGA AGAACCTGCA GCAGTACCAT CCCACTGATA    2640
```

```
TCACGGGCCC GCTCAACCTC TCAGATCCCT CGGTCAGCAC CGTGGTGTGA GGCCCCCGGA        2700

GCGCCCACCT GCCCAGTTTA GCCCGGC                                           2727
```

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

```
GACCCCAGGC TCAGAATTCC CTCAGACAAG                                          30
```

(2) INFORMATION FOR SEQ ID NO:15:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

```
CACCAGGAAG AAGTCTGCCA TGTTCTCA                                            28
```

(2) INFORMATION FOR SEQ ID NO:16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

```
TGCCGGGAAT TCTGGTCTGG CGCGATCCGG                                          30
```

(2) INFORMATION FOR SEQ ID NO:17:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

```
GGGTCAAGCT TTTCATCAAT AACGCCAC                                            28
```

(2) INFORMATION FOR SEQ ID NO:18:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

```
TGCTAAGATT CTTCGGTCAG CTAAAAAC                                            28
```

(2) INFORMATION FOR SEQ ID NO:19:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

AATGTGAAGC TTTCTGCCGG TATCGATCAC                                        30

(2) INFORMATION FOR SEQ ID NO:20:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

CCCCACTGCA TCCGGTACCT TCTCGGGCTA CA                                     32

(2) INFORMATION FOR SEQ ID NO:21:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

AGTCCCAGTC ATATGAGACA GAAATGA                                           27